United States Patent
Meier

(10) Patent No.: US 11,141,424 B2
(45) Date of Patent: Oct. 12, 2021

(54) BLADDER INSTILLATION COMPOSITION CONTAINING CHONDROITIN SULFATE (20 MG/ML), HYALURONIC ACID (16 MG/ML) AND A PHOSPHATE BUFFER (PH 6.1 TO 7.9) WITH INCREASED STORAGE STABILITY FOR TREATING CYSTITIS

(71) Applicant: Farco-Pharma GmbH, Cologne (DE)

(72) Inventor: Andreas Meier, Cologne (DE)

(73) Assignee: FARCO-PHARMA GMBH, Cologne (DE)

( * ) Notice: Subject to any disclaimer, the term of this patent is extended or adjusted under 35 U.S.C. 154(b) by 91 days.

(21) Appl. No.: 16/612,011

(22) PCT Filed: May 2, 2018

(86) PCT No.: PCT/EP2018/061147
§ 371 (c)(1),
(2) Date: Nov. 8, 2019

(87) PCT Pub. No.: WO2018/206357
PCT Pub. Date: Nov. 15, 2018

(65) Prior Publication Data
US 2021/0137968 A1    May 13, 2021

(30) Foreign Application Priority Data

May 12, 2017 (EP) .................................. 17000820
May 31, 2017 (EP) .................................. 17173817

(51) Int. Cl.
| | | |
|---|---|---|
| A61K 31/728 | (2006.01) | |
| A61P 13/10 | (2006.01) | |
| A61K 31/737 | (2006.01) | |
| A61K 47/02 | (2006.01) | |
| A61M 3/02 | (2006.01) | |
| A61K 9/00 | (2006.01) | |
| A61K 9/08 | (2006.01) | |

(52) U.S. Cl.
CPC .......... *A61K 31/728* (2013.01); *A61K 9/0034* (2013.01); *A61K 9/08* (2013.01); *A61K 31/737* (2013.01); *A61K 47/02* (2013.01); *A61M 3/0266* (2013.01); *A61P 13/10* (2018.01)

(58) Field of Classification Search
CPC .. A61K 9/0034; A61K 31/728; A61K 31/737; A61P 13/00–12
See application file for complete search history.

(56) References Cited

U.S. PATENT DOCUMENTS 7,820,194 B2 * 10/2010 Jafari ................... A61K 31/716
424/427

FOREIGN PATENT DOCUMENTS

| CN | 105982912 | 10/2016 | |
|---|---|---|---|
| WO | 2007138014 | 12/2007 | |
| WO | WO-2008071245 A1 * | 6/2008 | ............. A61P 13/00 |
| WO | 2013144867 | 10/2013 | |

OTHER PUBLICATIONS

Machine translation of WO 2008/071245. (Year: 2008).*
Marcellin, E. et al "Insight into hyaluronic acid molecular weight control" Appl. Microbiol. Biotechnol., vol. 98, pp. 6947-6956. (Year: 2014).*
Pyo et al.; Systematic Review and Meta-Analysis of Intravesical Hyaluronic Acid and Hyaluronic Acid/Chondroitin Sulfate Instillation for Interstitial Cystitis/Painful Bladder Syndrome; Cellular Physiology and Biochemistry, vol. 39, No. 4, pp. 1618-1625; Sep. 2016.
Anonymous; iAluRil(R): Product Information; Juno Pharmaceuticals; URL:http://www.ialuril.com.au/downloads/iAluRil-Product-Information-JUNO-Aus-Oct-10- 2015.pdf; Oct. 2015.

* cited by examiner

*Primary Examiner* — Leigh C Maier
(74) *Attorney, Agent, or Firm* — Edward E. Sowers; Brannon Sowers & Cracraft PC

(57) ABSTRACT

The invention relates to a composition, in particular a pharmaceutical composition, which is suitable in particular for the prophylactic and/or therapeutic treatment preferably of inflammatory diseases of the urogenital tract, in particular inflammatory diseases of the bladder, preferably cystitis, to the uses thereof, to a storage or application device relating to same, to a packaging unit, and finally to a kit which is designed in particular as an instillation system.

20 Claims, No Drawings

BLADDER INSTILLATION COMPOSITION CONTAINING CHONDROITIN SULFATE (20 MG/ML), HYALURONIC ACID (16 MG/ML) AND A PHOSPHATE BUFFER (PH 6.1 TO 7.9) WITH INCREASED STORAGE STABILITY FOR TREATING CYSTITIS

CROSS-REFERENCES TO RELATED APPLICATIONS

This application is a National Stage filing of International Application PCT/EP 2018/061147, filed May 2, 2018, entitled BLADDER INSTILLATION COMPOSITION CONTAINING CHONDROITIN SULFATE (20 MG/ML), HYALURONIC ACID (16 MG/ML) AND A PHOSPHATE BUFFER (PH 6.1 TO 7.9) WITH INCREASED STORAGE STABILITY FOR TREATING CYSTITIS, claiming priority to EP 17 000 820.5, filed May 12, 2017, and to EP 17 173 817.2, filed May 31, 2017. The subject application claims priority to PCT/EP 2018/061147, EP 17 000 820.5 and to EP 17 173 817.2 and incorporates all by reference herein, in their entirety.

BACKGROUND OF THE INVENTION

The present invention relates to the medical therapeutic area of the treatment of preferably inflammatory diseases of the urogenital tract, especially cystitis, such as interstitial cystitis.

In particular, the present invention relates to a composition, especially pharmaceutical composition, which is especially suitable for the prophylactic and/or therapeutic treatment of preferably inflammatory diseases of the urogenital tract, especially of inflammatory diseases of the bladder, preferably of cystitis. Likewise, the present invention also relates to corresponding uses of the composition according to the invention and to a storage and/or application device containing the composition according to the invention. The present invention also relates to a package unit containing the storage and/or application device according to the invention and to a kit containing the storage and/or application device according to the invention, the composition according to the invention and an instillation device connectable to the storage and/or application device.

The clinical picture of cystitis can generally be divided into two groups. Besides a cystitis of the kind which is caused by bacterial infections in particular and which can generally be therapied using antibiotics or else by surgical intervention to eliminate causes of the infection, for example in the case of obstructions or reflux, there is a range of inflammations of the bladder that are not caused by infections. These include radiation cystitis and interstitial cystitis.

Radiation cystitis occurs in approx. 5% of patients irradiated in the lesser pelvis because of malignancies. This hemorrhagic cystitis generally occurs six months to ten years after the irradiation and may be attributed to probably irreversible tissue changes.

The treatment options in the case of radiation cystitis encompass a therapy with antispasmodics, for example trospium chloride, darifenacin, etc., or a so-called hyperbaric oxygenation.

A far larger field is interstitial cystitis, especially since this affects a large circle of individuals. Interstitial cystitis is sometimes also defined as "chronic idiopathic bladder inflammation of uncertain genesis". Interstitial cystitis is difficult to diagnose, and its treatment options are regarded as challenging. Interstitial cystitis is also subsumed under the expression "painful bladder syndrome".

With respect to etiology, there are sometimes still no completely reliable findings. In this regard, various hypotheses are under discussion, such as a release of inflammatory substances due to mast cell activation owing to different stimuli; occult infections; increase in the permeability of the bladder wall for toxic substances; immunological processes and also a hypersensitivity of nerve fibers with increase in nerve fiber density.

Besides urination record and pain diary with VAS (visual analog scale) and besides bacteriological testing to rule out a urinary tract infection and urine cystology to rule out a carcinoma in situ, the diagnostic spectrum for interstitial cystitis encompasses cystoscopy to be carried out under anesthesia with or without associated biopsy.

Interstitial cystitis is a chronic inflammatory disease of the bladder without any detectable bacteria in the urine. Consequently, what is concerned here is cystitis of nonbacterial origin. It is a disease which has not been fully explained to date, and patients often suffer worse from said disease than from a tumor disease. The US National Health Institute has also classified interstitial cystitis as a higher-priority disease. Quality of life can be extremely impaired by severe urinary urgency, frequent urination during the day and at night, and increasing pain.

According to the latest surveys, the incidence of the disease appears to be increasing. Patients in whom the disease occurs are usually middle-aged. The disease occurs proportionally more frequently in women than in men. One reason therefor can be seen in the anatomy of a woman, whose urethra is shorter than that of a man. This leads to a higher susceptibility to rising urinary tract infections. In the case of women with repeated (recurrent) urinary tract infections, the bladder mucosa is damaged to a greater extent This constant irritation can lead to nonbacterial, especially chronic interstitial cystitis. Interstitial cystitis is thus predominantly diagnosed in women, though men can also be affected by the disease.

The most common symptoms of interstitial cystitis are (ordered from most common to least common):
 increased urinary urgency;
 frequent urination;
 pain in the pelvis, the lower abdomen and the intestines;
 pelvic pressure;
 pain during urination, associated with release of tiniest amounts of urine;
 severe pain during and after sexual intercourse;
 burning sensation of pain;
 severe problems in sleeping through the night due to pain;
 blood in urine.

The major symptoms of interstitial cystitis are thus a loss of bladder capacity with fill-dependent pain and with frequent and severe urinary urgency. Reference is also made to the triad: "frequency, urgency, pain".

The aforementioned symptoms of interstitial cystitis can, for example, additionally increase as a result of increased pain sensitivity or as a result of psychological factors. A disturbance in the composition of the glycosaminoglycan layer has been shown, and immunohistochemical tests show inter alia reduced chondroitin sulfate staining.

Without wishing to be restricted or tied to any theory, the formation and development of an interstitial cystitis can be explained as follows: through gaps in the protective layer of the bladder mucosa, the so-called glycosaminoglycan layer, bacteria, microcrystals, proteins and/or harmful, dissolved urine constituents, such as urea, get directly into deeper layers of the bladder mucosa, where they bring about further damage.

The damage to the bladder mucosa and the resulting chronic inflammation lead to repair processes, which are often associated with scarring. This can lead to a reduced elasticity of the bladder wall and to an increasing loss in the capacity of the bladder. In the late stage of interstitial cystitis, a contracted bladder may arise, and a surgical removal of the bladder may be necessary under certain circumstances. Therefore, an early identification and therapy to avoid the late stage of interstitial cystitis is of great importance.

The main cause of interstitial cystitis is the damage to the bladder mucosa. A protective layer containing inter alia hyaluronic acid shields the bladder mucosa against microorganisms, cancer-causing substances, and other harmful substances which occur in urine. Said protective layer, which is also referred to as glycosaminoglycan layer (GAG layer) and which contains not only hyaluronic acid, but also chondroitin sulfate, heparin and pentosan polyphosphate as important constituents, is extremely hydrophilic and forms so to speak a "water film" and thus a further physical barrier against damaging substances in urine as well.

In patients with cystitis and especially with interstitial cystitis, there are defects in this protective layer of the bladder mucosa. In particular, a loss of hyaluronic acid has been established.

Further causes of interstitial cystitis can be, for example, autoimmune reactions, which are directed to endogenous cells in the bladder, or previous chronic bacterial infections.

The typical symptoms of interstitial cystitis are frequent urination, increased urinary urgency and, in some cases, also an uncontrolled urination (urinary incontinence) and blood in urine. Severe pain develops especially in a full bladder; a decrease in the sensation of pain after urination is typical. Further signs are pain in the pelvis, the lower abdomen and the intestines, pelvic pressure and also pain during urination, associated with urine being able to be released only in drops. Severe pain frequently occurs during and after sexual intercourse as well. In many cases, patient complaints involve such a tremendous level of suffering that even surgical procedures culminating in cystectomy are necessary.

To diagnose interstitial cystitis, it is important that other bladder diseases with similar symptoms can be ruled out. In a first step, it should be clarified whether the patient is suffering pain as a result of an earlier operation (e.g., in the lower abdomen), whether the bladder inflammation has been caused by a radiation therapy or chemotherapy or whether there were or there are repeated, recurrent infections. Consequently, it is necessary to test whether gynecological, neurological, psychiatric and/or rheumatic diseases can be ruled out. Furthermore, spinal complaints and allergies should be ruled out As part of interstitial cystitis testing or diagnosis, it is, for example, possible to carry out a urine culture and testing of the cellular constituents in the urine (urine cytology) in a laboratory. In the case of female patients, a vaginal smear should be done to rule out sexually transmittable diseases.

Pain sensitivity is gathered by palpation of the vagina. In the case of male patients, a bacterial culture is prepared from the ejaculate to rule out a prostate inflammation caused by bacteria. To rule out a prostate cancer, the value of the prostate-specific tumor marker (PSA=prostate-specific antigen) is determined. By means of an ultrasound examination, residual urine is determined and an inward growth of the prostate into the bladder is ruled out.

A further examination can also be carried out by means of a cystoscopy. Cystoscopy can be carried out under anesthesia. Typical signs of an interstitial cystitis, which can be manifested by means of the cystoscopy, are increased inward growth of blood vessels into the bladder mucosa, liquid accumulations in the mucosa, rupture of the mucosa (glomeruli), point-shaped bleedings after expansion of the bladder under pressure due to inward flushing of water (hydrodistention) and also, in about 10 to 20% of patients, signs of bladder ulcers (Hunner's ulcers).

In interstitial cystitis, patients already feel a severe urinary urgency with small amounts of urine; their bladder capacity is reduced. To diagnose interstitial cystitis, it is therefore possible to determine the maximum fill volume and to then do a comparative bladder-capacity measurement (cystometry).

Investigations in relation to interstitial cystitis show that the bladder epithelium or the urothelium of the bladder is deficient when there is a cystitis. This weakening substantially contributes to the clinical symptoms of interstitial cystitis.

In terms of the therapy of interstitial cystitis, there is hitherto neither a remedy nor a treatment method that is effective for all patients.

For instance, a composition based on pentosan polysulfate sodium is known in the prior art It is assumed that the mode of action consists in the repair of a thin or damaged bladder wall. The outcomes are, however, not always satisfactory.

Antidepressants too, such as tricyclic antidepressants, have been found in some ways to be effective for alleviating pain and frequency of urination in interstitial cystitis. However, these medicaments are only used in interstitial cystitis because of their pain-relieving properties.

Further oral drugs encompass anti-inflammatories, antispasmodics, antihistamines and muscle relaxants. However, such medicaments can alleviate the disease only to a certain extent. A decisive therapeutic success is generally not possible with these medicaments.

Furthermore, it is possible to carry out bladder instillations with certain substances. Thus, bladder stretching can be realized, involving filling the bladder with water under a general anesthetic to achieve stretching. Although this is one of the primary diagnostic methods for interstitial cystitis, it can also be used therapeutically.

Furthermore, DMSO (dimethyl sulfoxide) can be directly filled into the bladder as a drug. It is intended to have an anti-inflammatory action and to thus reduce pain. DMSO can be mixed with steroids, heparin and other ingredients to form a "bladder cocktail". However, the adverse effects are often high.

Other bladder instillations, for example using oxychlorosene sodium, are for the most part very painful and require a general anesthetic. Silver nitrate is rarely used and is considered to be outdated therapy.

Other treatment methods, such as a specific diet involving avoidance of certain foodstuffs, especially acidic, spicy foodstuffs, can alleviate the severity of the symptoms only slightly. Interstitial cystitis can also be aggravated by smoking, coffee or tea, and alcoholic beverages.

Self-help techniques can make a small improvement to quality of life and can reduce the incidence and severity of attacks. These include, for example, a change in lifestyle, stress reduction, visualization, biofeedback, bladder training and sporting activity. However, a permanent therapeutic success is often not possible with these methods.

For a small number of patients with severe symptoms which do not respond to other treatment methods, a bladder operation can be contemplated. However, in some cases, the symptoms do not become better either as a result. To treat interstitial cystitis, several types of operations have been used, including cystectomy and urinary diversion. However, owing to the severity of surgical intervention, operations should always be the last resort.

The therapeutic options are thus as diverse as they are unsatisfactory overall. In summary and in addition to the above remarks, the following treatment methods for interstitial cystitis are possible to date. Medicaments which influence innervation (antispasmodics, antihistamines); a cytodestructive therapy with subsequent regeneration (e.g., DMSO, hydrodistention); a cytoprotective therapy to restore the glycosaminoglycan layer (heparin, pentosan polysulfate). Conservative therapy involves the reduction of symptoms by means of orally administered substances, such as antispasmodics (success: low); antihistamines; antidepressants, especially tricyclics (amitriptyline); cytoprotectants, such as pentosan polysulfate (very long latency of up to two years until success is measurable); immunosuppressants, such as azathioprine, cyclosporine, chloroquine; calcium antagonists, for example nifedipine. Hydrodistention is the overstretching of the bladder by means of an intravesically introduced balloon. Generally, stretching is carried out over a period of three hours, but the therapeutic effect is low and only short-lasting. Furthermore, there are various intravesical pharmacotherapeutic measures, especially for restoring the glycosaminoglycan layer. As discussed above, pentosan polysulfate, heparin or DMSO are used for this purpose. Alternative treatment methods are carried out, too. These include relaxation exercises, behavioral training, acupuncture, neuromodulation and dietary measures.

In the prior art, further compositions or methods are proposed for the treatment of cystitis, such as interstitial cystitis; however, these do not always have the desired or required efficiency of action. Moreover, such prior-art compositions are sometimes not sufficiently storage-stable.

WO 2004/073584 A2 relates to a pharmaceutical composition for insertion into the bladder of a patient, wherein the composition comprises chondroitin sulfate. This document focuses on the use of an individual active ingredient.

Furthermore, U.S. Pat. No. 6,083,933 A relates to compositions which contain chondroitin sulfate and which can be used in the context of the treatment of interstitial cystitis. However, the action with respect to the cystitides to be treated is not always adequate owing to the use of a mono-composition which, apart from chondroitin sulfate, does not contain any further active ingredients.

U.S. Pat. No. 5,880,108 A1 relates to a method for treating cystitis, wherein the bladder and the structures associated therewith are intended to be contacted with a solution, the solution comprising hyaluronic acid. The composition can furthermore contain certain substances which are intended to be suitable for the treatment of underlying diseases associated with cystitis.

With respect to the medical therapeutic demands on relevant instillation compositions and the handleability thereof, there is in the prior art, besides the provision of a high efficacy with regard to the underlying disease, additionally a great need for stable compositions or for compositions with a long shelf life, i.e., for those instillation compositions which have defined or constant (product) properties over an appropriately long period, for example with respect to the stability of the active substances with associated small amounts of sometimes toxic degradation products, pH stability, constant viscosity or the like. In particular, there is a corresponding need for compositions with high storage stability, i.e., those instillation compositions which are stable or constant, even over a long period, with respect to their ingredients and active ingredients and their physicochemical properties.

This is because compositions which are known from the prior art and which are administered in the context of the treatment of especially inflammatory diseases of the urogenital tract, such as cystitis, sometimes exhibit stability behaviors which are not optimal, there additionally being an efficacy which is not always optimal. In this connection, there is especially also a risk that sometimes prematurely degraded compositions with possibly a reduced amount of active ingredient and with a correspondingly increased proportion of possibly harmful degradation products are used in the context of the underlying treatment, which, however, may be detrimental to a decisive success of treatment.

BRIEF SUMMARY OF THE INVENTION

Against this background, it is therefore an object of the present invention to provide a relevant composition, especially pharmaceutical composition, preferably for the prophylactic and/or therapeutic treatment of preferably inflammatory diseases of the urogenital tract, for example cystitis, especially interstitial cystitis, which composition at least largely avoids or else at least diminishes the above-described disadvantages of the prior art.

In particular, such a composition is to have—if compared to conventional pharmaceutical compositions or preparations intended for the treatment of especially inflammatory diseases of the urogenital tract, especially cystitis, such as interstitial cystitis—an improved stability, especially storage stability, especially with respect to active-ingredient amounts and physicochemical properties of the underlying compositions that are constant even over relatively long periods.

Furthermore, it is in turn a further object of the present invention to also provide a relevant composition which moreover has a high efficiency of action in the treatment of preferably inflammatory diseases of the urogenital tract, especially cystitis, such as interstitial cystitis, and the handleability and compatibility thereof are likewise to be further improved.

To achieve the above-described object, the present invention proposes—according to a first aspect of the present invention—a composition, especially pharmaceutical composition, as described herein; further, especially advantageous configurations of the composition according to the invention are further described.

Furthermore, the present invention provides—according to a second aspect of the present invention—also the use of the composition according to the invention.

Moreover, the present invention provides—according to a third aspect of the present invention—a storage and/or application device comprising or containing the composition according to the invention, as defined in the relevant independent claim concerning the storage and/or application device; further, especially advantageous configurations of the storage and/or application device according to the invention are the subject matter of the relevant dependent claim.

Furthermore, the present invention provides—according to a fourth aspect of the present invention—also a package unit containing the storage and/or application device according to the invention, as claimed in the relevant independent claim concerning the package unit Lastly, the present invention provides—according to a fifth aspect of the present invention—also a kit, especially instillation system, as defined in the independent claim concerning the kit.

It is understood in connection with the remarks that follow that configurations, embodiments, advantages and the like which are stated below only in relation to one aspect of the invention for the purposes of avoiding repetition self-evidently also apply mutatis mutandis with respect to the other aspects of the invention, without this requiring a separate mention.

In the case of all below-mentioned relative or percentage weight-based data, especially quantity data, it should be further noted that they can be selected by a person skilled in the art in the context of the present invention such that they always make up or add up to 100% or 100% by weight in the sum total with inclusion of all components or ingredients, especially as defined below; this is, however, understood by a person skilled in the art.

Furthermore, a person skilled in the art—depending on the application or the particular case—can deviate from the concentration, weight, quantity and range data stated below, without departing from the scope of the present invention.

Moreover, all below-mentioned value data or parameter data or the like can fundamentally be ascertained or determined using standardized or explicitly specified methods of determination or otherwise using methods of determination or measurement that are familiar per se to a person skilled in the art in this field.

The term of drug or medicament (also synonymously "pharmaceutical"), as used in the context of the present invention, is to be understood in a very extensive manner and encompasses not only drugs or pharmaceuticals as such (i.e., with respect to drug legislation), but also especially so-called medical devices as well and furthermore but also homeopathic products and food supplements and also cosmetics and articles of daily use. In other words, the composition according to the invention can thus be present in the form of a drug (pharmaceutical), medical device, homeopathic product, food supplement, cosmetic or in the form of an article of daily use.

This said, the present invention will now be elucidated below in detail.

DETAILED DESCRIPTION OF THE INVENTION

The present invention thus provides—according to a first aspect of the present invention—a composition, especially pharmaceutical composition, preferably for the prophylactic and/or therapeutic treatment of preferably inflammatory diseases of the urogenital tract, especially of inflammatory diseases of the bladder, preferably of cystitis, such as interstitial cystitis, wherein the composition contains
  (a) chondroitin sulfate and/or a physiologically compatible chondroitin sulfate salt in a concentration of (20±2) mg/ml (component (a));
  (b) hyaluronic acid and/or a physiologically compatible hyaluronic acid salt (hyaluronate) in a concentration of (16±1.6) mg/ml (component (b));
  (c) a dihydrogen phosphate/monohydrogen phosphate buffer system (component (c));
  (d) optionally at least one physiologically compatible electrolyte (component (d)); in combination and, in each case, in effective, especially pharmaceutically effective, amounts,
wherein the composition has a pH within the range from 6.1 to 7.9 and/or wherein the composition is set to a pH within the range from 6.1 to 7.9.

In the context of the present invention, it has been surprisingly found that it is possible to provide on the basis of the concept of the invention a specific composition—containing specifically chondroitin sulfate and/or a physiologically compatible chondroitin sulfate salt having a defined concentration as component (a), hyaluronic acid and/or a physiologically compatible hyaluronic acid salt (also synonymously referred to as "hyaluronate") having a defined concentration as component (b), a dihydrogen phosphate/monohydrogen phosphate buffer system (also synonymously referred to as "$H_2PO_4^-/HPO_4^{2-}$ buffer (system)" or "phosphate buffer (system)" or chemical buffer system) as component (c) and also optionally at least one physiologically compatible electrolyte as component (d), the composition moreover having a pH which is defined and is set and/or maintained by means of the chemical buffer system—for purposeful application, especially instillation, in the context of the treatment of preferably inflammatory diseases of the urogenital tract, such as cystitis, especially interstitial cystitis, which composition has, compared to the prior art, additionally an improved stability, especially storage stability, with a high efficacy or efficiency of action and a very good compatibility at the same time.

What is provided on the basis of the composition according to the invention is consequently a high-potency drug or medicament or (medical) device which has an outstanding stability, especially storage stability, owing to the specific combination and harmonization of the underlying components and to the setting of a defined pH, there being, even after appropriately long storage periods, no substantial degradation of the ingredients and active ingredients that has an adverse effect on efficacy and on compatibility, the physicochemical properties and the efficacy of the composition additionally also remaining at least substantially unchanged.

Concerning the improvement in stability, especially storage stability, completely surprisingly found in the context of the present invention with a high efficacy of the composition according to the invention at the same time, what is of great importance in this regard is also the concentrations of components (a) and (b) that are present in the composition according to the invention. This is because the applicant has found in this connection that there is a relevant stability and activity optimum on the basis of the concentrations provided according to the invention and the associated substance amounts, especially on the basis of components (a) and (b).

In addition, the inventive measures with respect, too, to the use of a specific buffer system as per component (c) and to the setting of a specific pH intertwine so to speak and reinforce each other and beyond the effect of the individual measures with respect to ensuring a high stability, especially storage stability, and efficacy, with the result that there is in this regard a synergistic effect, as also shown on the basis of the exemplary embodiments stated below. Without wishing to be restricted or tied to the theory which follows, there is with respect to the composition according to the invention as a result of the relevant measures, as stated above, so to speak an optimal formation of a matrix or hydrogel based on the underlying components, especially with respect to the components (a) and (b), and this counteracts the degradation of the underlying ingredients and active ingredients and a storage- and time-dependent change in the physicochemical properties, such as viscosity or the like. Consequently, there is a corresponding increase in stability, associated with long storage periods.

In the context of the present invention, the chemical buffer system as per component (c) serves especially for the stabilization of the composition according to the invention. In particular, the setting of a constant pH by means of the buffer system surprisingly leads to efficient counteracting of an undesired degradation of the active ingredients, especially of components (a) and (b), during storage even over a relatively long period. In this way, the stability or storability of the composition according to the invention is improved.

With respect to stability behavior, it has moreover been completely surprisingly found in the context of the present invention that the use of a specific phosphate buffer (system) as per component (c) is superior to other buffers or buffer systems, meaning that there is a further improvement in the underlying stability properties as a result of the use of the specific phosphate buffer (system). Likewise without wishing to be restricted or tied to this theory, the use of a specific buffer also leads to a further stabilization of the matrix resulting from components (a) and (b) or of the relevant hydrogel, specifically also due to the fact that there is, on the basis of the specific buffer system, a pH stabilization which is optimal in this regard, and this is altogether beneficial for the stability of the composition.

Furthermore, the composition according to the invention is also distinguished by an outstanding efficacy or efficiency of action with a good compatibility at the same time with respect to the treatment of preferably inflammatory diseases of the urogenital tract, especially cystitis, such as interstitial cystitis. Owing to the defined and constant, even after long storage periods, physicochemical properties of the composition according to the invention, there is moreover improvement in handling and application, especially with respect to instillation into the bladder, and this also leads to an increased acceptance by the patient and to a reduction of misuses.

On the basis of the concept of the invention, there is altogether counteracting of a degradation over time and a degradation dependent on time of the relevant ingredients and active ingredients, especially also with respect to components (a) and (b), with the result that there are high and constant active-ingredient concentrations at a pH which is constant over time, even after appropriately long periods. As a result, what is moreover ensured is that sometimes toxic or harmful degradation products are not present or are only present in small amounts, and this likewise can be judged to be positive for the efficiency of action and compatibility of the composition according to the invention.

Altogether, what is thus provided on the basis of the concept of the invention is a composition which is outstandingly suitable for the treatment of preferably inflammatory diseases of the urogenital tract, such as cystitis, and has significantly improved properties compared to the prior art.

Concerning component (a) in the form of chondroitin sulfate and/or the physiologically compatible chondroitin sulfate salt (also synonymously referred to as chondroitin polysulfate and chondroitin polysulfate salt, respectively) as used according to the invention, it has been found to be advantageous according to the invention when the composition comprises or contains the chondroitin sulfate and/or the physiologically compatible chondroitin sulfate salt (component (a)) in a concentration of (20±1.5) mg/ml, especially in a concentration of (20±1) mg/ml, preferably in a concentration of (20±0.5) mg/ml, particularly preferably in a concentration of about 20 mg/ml. In particular, the applicant has found that, as stated above, there is an appropriate stability and efficacy maximum with respect to the composition according to the invention with regard to the discussed concentration ranges - especially also in cooperation with component (b).

Furthermore, the molecular weight (also synonymously referred to as "molar mass") of component (a) is also of great importance:

Thus, what can be provided according to the invention is that the chondroitin sulfate and/or the physiologically compatible chondroitin sulfate salt (component (a)) has a number-average molecular weight (molar mass) $M_n$ within the range from 2 kDa to 200 kDa, especially within the range from 5 kDa to 150 kDa, preferably within the range from 10 kDa to 100 kDa, by preference within the range from 12 kDa to 75 kDa.

In particular, the chondroitin sulfate and/or the physiologically compatible chondroitin sulfate salt (component (a)) can have a weight-average molecular weight (molar mass) $M_w$ within the range from 10 kDa to 200 kDa, especially within the range from 15 kDa to 175 kDa, preferably within the range from 20 kDa to 150 kDa, by preference within the range from 30 kDa to 120 kDa.

Moreover, the chondroitin sulfate and/or the physiologically compatible chondroitin sulfate salt (component (a)) can have a centrifuge-average molecular weight (molar mass) $M_z$ within the range from 30 kDa to 1000 kDa, especially within the range from 40 kDa to 800 kDa, preferably within the range from 50 kDa to 600 kDa, by preference within the range from 100 kDa to 450 kDa.

In this connection, the polydispersity index (PDI) is also of relevant importance: In this regard, what can be provided according to the invention is that the chondroitin sulfate and/or the physiologically compatible chondroitin sulfate salt (component (a)) has a polydispersity index (PDI), calculated as the quotient of weight-average molecular weight $M_w$ and number-average molecular weight $M_n$ ($M_w:M_n$), of at least 1, especially at least 1.2, preferably at least 1.5, by preference at least 2.

Moreover, the chondroitin sulfate and/or the physiologically compatible chondroitin sulfate salt (component (a)) can have a polydispersity index (PDI), calculated as the quotient of weight-average molecular weight $M_w$ and number-average molecular weight $M_n$, of at most 30, especially at most 20, preferably at most 10, by preference at most 8.

Furthermore, the chondroitin sulfate and/or the physiologically compatible chondroitin sulfate salt (component (a)) can have a polydispersity index (PDI), calculated as the quotient of weight-average molecular weight $M_w$ and number-average molecular weight $M_n$, within the range from 1 to 30, especially within the range from 1.2 to 20, preferably within the range from 1.5 to 10, by preference within the range from 2 to 8.

The aforementioned properties of component (a) with respect to the molecular weight or the molar mass or the relevant polydispersity index lead - without wishing to be restricted or tied to this theory - to a further improved formation of the matrix underlying the composition according to the invention, especially also with respect to the formation of a hydrogel, with corresponding stabilization of the particular ingredients and active ingredients. Likewise, the discussed molecular weights or molar masses with regard to component (a) also lead to a good efficiency of action of the composition according to the invention with respect to the underlying disease, especially—likewise without wishing to be restricted or tied to this theory—as a result of a good or optimal interaction with or good or optimal adhesion to the urothelium of the bladder.

Without wishing to be restricted or tied to any theory in this regard, this specific chondroitin sulfate is, owing to its molecular structure, particularly suitable—especially in conjunction with component (b)—for regenerating or for filling to some extent the glycosaminoglycan layer of the urothelium, resulting in the lowering of the permeability of this layer. This increases the protective function of the glycosaminoglycan layer or of the mucus layer of the urothelium (mucin layer), with the result that a distinct alleviation or even healing of the disease symptoms can occur.

Concerning the determination of the molecular weight of component (a) as used according to the invention, what is determined is the number-average molecular weight $M_n$ and/or the weight-average molecular weight $M_w$ and/or the centrifuge-average molecular weight $M_z$ and/or the polydispersity index (PDI) of the chondroitin sulfate and/or of the physiologically compatible chondroitin sulfate salt (component (a)), especially by means of gel-permeation chromatography (GPC) and/or in accordance with DIN 55672-3: 2016-03.

In particular, it is possible to determine the number-average molecular weight $M_n$ and/or the weight-average molecular weight $M_w$ and/or the centrifuge-average molecular weight $M_z$ and/or the polydispersity index (PDI) of the chondroitin sulfate and/or of the physiologically compatible chondroitin sulfate salt (component (a)) by means of gel-permeation chromatography (GPC), especially at a temperature within the range from 20° C. to 40° C. and/or with 0.1 mol/l NaCl solution in deionized water as eluent and/or on a solution of chondroitin sulfate and/or of the physiologically compatible chondroitin sulfate salt having a concentration of 3 g/l and/or with use of a dextran/pullulan standard as calibration reagent, and/or in accordance with DIN 55672-3:2016-03.

Preferably according to the invention, the chondroitin sulfate and/or the physiologically compatible chondroitin sulfate salt (component (a)) can be of marine origin. In this regard, the chondroitin sulfate and/or the physiologically compatible chondroitin sulfate salt (component (a)) can be obtained from cartilaginous fish, especially sharks, preferably shark cartilage. In this regard, the applicant has completely surprisingly found that such a chondroitin sulfate of marine origin leads to particularly good results especially in the treatment of preferably inflammatory diseases of the urogenital tract, such as cystitis, especially when this is used in purposeful combination with the hyaluronic acid as per component (b). The relevant isolation of the active substances is familiar as such to a person skilled in the art, and so there is no need for further remarks in this regard.

According to the invention, what is especially provided is that the chondroitin sulfate and/or the physiologically compatible chondroitin sulfate salt (component (a)) is present in the form of an alkali metal salt, preferably in the form of a sodium salt, and this leads to particularly good results in the context of the present invention.

According to the invention, the chondroitin sulfate and/or the physiologically compatible chondroitin sulfate salt (component (a)) can preferably be present in the form of chondroitin sulfate sodium.

According to the invention, the chondroitin sulfate and/or the physiologically compatible chondroitin sulfate salt (component (a)) can moreover be selected from the group of chondroitin 4-sulfate, chondroitin 6-sulfate, chondroitin 2,6-sulfate, chondroitin 4,6-sulfate and combinations or mixtures thereof, preferably chondroitin 2,6-sulfate (chondroitin sulfate D). The aforementioned specific chondroitin sulfates, too, are preferably used according to the invention in the form of their alkali metal salts, preferably sodium salts, and this is associated with particularly good results with respect to the treatment of preferably inflammatory diseases of the urogenital tract, such as cystitis.

In the context of the present invention, component (a) of the composition according to the invention can preferably be based on a sterile and/or high-purity solution or suspension, especially of the sodium salt of chondroitin sulfate.

Chondroitin sulfate and/or chondroitin sulfate salt usable in the context of the present invention is generally commercially available, for example from Nexira, Rouen (FR), Artesan Pharma GmbH & Co. KG or from Pharma Greven GmbH, Greven (DE).

For further details in relation to the term of chondroitin sulfates, reference can be made to RÖMPP Chemielexikon [Römpp's Chemistry Lexicon], 10th edition, volume 1, 1996, Georg Thieme Verlag Stuttgart/New York, page 736, keyword: "chondroitin sulfates", and to the literature cited therein, the entire disclosure content of the aforementioned literature being hereby fully incorporated by reference.

Concerning the further component in the form of the hyaluronic acid and/or the physiologically compatible hyaluronic acid salt as per component (b) that is used for the composition according to the invention, the following in particular can be stated in this regard:

According to the invention, what can be provided in general is that the composition contains the hyaluronic acid and/or the physiologically compatible hyaluronic acid salt (component (b)) in a concentration of (16±1.2) mg/ml, especially in a concentration of (16±0.8) mg/ml, preferably in a concentration of (16±0.4) mg/ml, particularly preferably in a concentration of about 16 mg/ml. Within the aforementioned concentration ranges, particularly good properties are obtained with respect to stability and efficacy, especially on the basis of an interaction especially with components (a) and/or (c) and with the specific pH of the composition according to the invention.

Especially with respect to stability, preferably storage stability, of the composition according to the invention and the efficacy thereof in the treatment of preferably inflammatory diseases of the urogenital tract, especially cystitis, preferably interstitial cystitis, particularly good results are moreover achieved when the hyaluronic acid has a specific molecular weight or a specific molar mass.

In this connection, it is preferred according to the invention when the hyaluronic acid and/or the physiologically compatible hyaluronic acid salt (component (b)) has a number-average molecular weight (molar mass) $M_n$ within the range from 10 kDa to 300 kDa, especially within the range from 20 kDa to 275 kDa, preferably within the range from 30 kDa to 260 kDa, by preference within the range from 50 kDa to 250 kDa, particularly preferably within the range from 75 kDa to 200 kDa.

In particular, the hyaluronic acid and/or the physiologically compatible hyaluronic acid salt (component (b)) can have a weight-average molecular weight (molar mass) $M_w$ within the range from 10 kDa to 500 kDa, especially within the range from 20 kDa to 450 kDa, preferably within the range from 50 kDa to 425 kDa, by preference within the range from 100 kDa to 400 kDa, particularly preferably within the range from 150 kDa to 395 kDa.

Furthermore, the hyaluronic acid and/or the physiologically compatible hyaluronic acid salt (component (b)) can have a centrifuge-average molecular weight (molar mass) $M_z$ within the range from 80 kDa to 1500 kDa, especially within the range from 100 kDa to 1250 kDa, preferably within the range from 200 kDa to 1000 kDa, by preference within the range from 300 kDa to 750 kDa.

The aforementioned molecular weights, especially in purposeful harmonization and combination with the corresponding molecular weights of component (a), result in a particularly good stabilization and efficiency of action of the composition according to the invention, especially since—without wishing to be restricted or tied to this theory—the aforementioned molecular weights ensure an optimal formation of matrix or hydrogel with corresponding stabilization and with further optimized interaction especially with the urothelium of the bladder.

In this regard, the polydispersity index of component (b) as used according to the invention is also of importance:

Thus, what can be provided according to the invention is that the hyaluronic acid and/or the physiologically compatible hyaluronic acid salt (component (b)) has a polydispersity index (PDI), calculated as the quotient of weight-average molecular weight $M_w$ and number-average molecular weight $M_n$, of at least 1, especially at least 1.1, preferably at least 1.2, by preference at least 1.3, particularly preferably at least 1.4.

In particular, the hyaluronic acid and/or the physiologically compatible hyaluronic acid salt (component (b)) can have a polydispersity index (PDI), calculated as the quotient of weight-average molecular weight $M_w$ and number-average molecular weight $M_n$, of at most 50, especially at most 25, preferably at most 10, by preference at most 5, particularly preferably at most 3.

Furthermore, what can be provided according to the invention is that the hyaluronic acid and/or the physiologically compatible hyaluronic acid salt (component (b)) has a polydispersity index (PDI), calculated as the quotient of weight-average molecular weight $M_w$ and number-average molecular weight $M_n$, within the range from 1 to 50, especially within the range from 1.1 to 25, preferably within the range from 1.2 to 10, by preference within the range from 1.3 to 5, particularly preferably within the range from 1.4 to 3.

The aforementioned molecular weights can be determined using methods known per se to a person skilled in the art. According to the invention, what can be determined is the number-average molecular weight $M_n$ and/or the weight-average molecular weight $M_w$ and/or the centrifuge-average molecular weight $M_z$ and/or the polydispersity index (PDI) of the hyaluronic acid and/or of the physiologically compatible hyaluronic acid salt (component (b)), especially by means of gel-permeation chromatography (GPC) and/or in accordance with DIN 55672-3:2016-03.

Moreover, it is possible to determine the number-average molecular weight $M_n$ and/or the weight-average molecular weight $M_w$ and/or the centrifuge-average molecular weight $M_z$ and/or the polydispersity index (PDI) of the hyaluronic acid and/or of the physiologically compatible hyaluronic acid salt (component (b)) by means of gel-permeation chromatography (GPC), especially at a temperature within the range from 20° C. to 40° C. and/or with 0.1 mol/l NaCl solution in deionized water as eluent and/or on a solution of hyaluronic acid and/or of the physiologically compatible hyaluronic acid salt having a concentration of 3 g/l and/or with use of a dextran/pullulan standard as calibration reagent, and/or in accordance with DIN 55672-3:2016-03.

According to the invention, what can be especially provided is that the ratio of the particular molecular weight $M_n$, $M_w$ or $M_z$ of chondroitin sulfate and/or of the physiologically compatible chondroitin sulfate salt (component (a)) to the corresponding molecular weight $M_n$, $M_w$ or $M_z$ of the hyaluronic acid and/or of the physiologically compatible hyaluronic acid salt (component (b)) is within a range from 1:3 to 1:4, especially 1:1 to 1:100, preferably 1:1.5 to 1:50, by preference 1:2 to 1:25, particularly preferably 1:3 to 1:10. The specific harmonization of the respective molecular weights or molar masses of component (a) and of component (b) yields particularly good results with respect to the stabilization and efficiency of action of the composition according to the invention, especially since—without wishing to be restricted or tied to this theory—there is in this regard a supplementation of action or a high compatibility of the discussed components (a) and (b) with one another.

According to the invention, what can moreover be especially provided is that the hyaluronic acid and/or the physiologically compatible hyaluronic acid salt (component (b)) is of nonanimal origin.

In this connection, the hyaluronic acid and/or the physiologically compatible hyaluronic acid salt (component (b)) can be of bacterial and/or fermentational origin. In this regard, the hyaluronic acid and/or the physiologically compatible hyaluronic acid salt (component (b)) can preferably be obtained by fermentation from bacteria of the genus *Streptococcus*, especially *Streptococcus lancefields*, preferably *Streptococcus lancefields* strain A. The relevant obtaining or isolation of the active substances is familiar as such to a person skilled in the art, and so there is no need for further remarks in this regard.

In this connection, the applicant has likewise surprisingly found out that the use of a nonanimal hyaluronic acid of the aforementioned type also significantly improves the pharmaceutical efficacy of the composition according to the invention with regard to the treatment of preferably inflammatory diseases of the bladder, such as cystitis, preferably interstitial cystitis. Without wishing to be restricted or tied to a specific theory, a possible reason therefor is that the nonanimal hyaluronic acid obtained especially from bacteria is a particularly pure product which has defined chemical and physical properties and which is highly potent. The defined formation of the hyaluronic acid of high purity is likewise also beneficial for the stability of the composition, since none of the impurities detrimental to stability is present. Moreover, the nonanimal hyaluronic acid is highly compatible, since there is no contamination or impureness with other substances, as is often the case with products obtained from animals. Thus, hyaluronic acid of nonanimal origin has a particularly high purity and homogeneity, and this is also beneficial for the stability, especially storage stability, of the composition according to the invention.

In one embodiment preferred according to the invention, the hyaluronic acid and/or the physiologically compatible hyaluronic acid salt (component (b)) can be present in the form of an alkali metal salt, preferably in the form of a sodium salt, and/or in the form of an alkali metal hyaluronate. In this connection, particularly good results are likewise obtained when the hyaluronic acid and/or the physiologically compatible hyaluronic acid salt (component (b)) is present in the form of sodium hyaluronate.

Component (b) of the composition according to the invention can be used especially on the basis of a sterile or high-purity solution or suspension, especially of the sodium salt of the hyaluronic acid.

Hyaluronic acid and/or hyaluronic acid salt usable in the context of the present invention is generally commercially available, for example from Vivatis Pharma GmbH, Hamburg (DE), Contipro S.A., Dolni Dobrouc (CZ) or from GFN Herstellung von Naturextrakten GmbH, Wald-Michelbach (DE).

For further details in relation to the term of hyaluronic acid and the physiologically compatible salts thereof, reference can be made to RÖMPP Chemielexikon [Römpp's Chemistry Lexicon], 10th edition, volume 3, 1997, Georg Thieme Verlag Stuttgart/New York, page 1820, keyword: "hyaluronic acid", and to the literature cited therein, the entire disclosure content of the aforementioned literature being hereby fully incorporated by reference.

According to the invention, what can moreover be provided is that, firstly, the chondroitin sulfate and/or the physiologically compatible chondroitin sulfate salt (component (a)) and, secondly, the hyaluronic acid and/or the physiologically compatible hyaluronic acid salt (component (b)) are present in the composition in a weight ratio (concentration ratio) of component (a) to component (b) [(a): (b)] within a range from 1:1 to 1.6:1, especially 1.1:1 to 1.5:1, preferably 1.2:1 to 1.4:1, particularly preferably about 1.25:1.

This is because the applicant has succeeded overall, through the specific matching and harmonization of the respective active substances based on components (a) and (b) with regard to the glycosaminoglycan layer of the bladder urothelium, in arriving at a particularly good efficacy with respect to the treatment of the underlying diseases, since—without wishing to be restricted or tied to a specific theory—there is especially in the case of the aforementioned quantitative ratios a particularly good interaction or integration of the active substances into the glycosaminoglycan layer of the bladder urothelium and a good regeneration of the glycosaminoglycan layer of the bladder urothelium, especially in connection with the aforementioned respectively specific molecular weights or molar masses of components (a) and (b). Consequently, as stated above, the permeability of the urothelium is significantly lowered, and this is associated with a distinct reduction in the symptoms associated with the underlying disease, especially cystitis, especially since irritants are no longer able to penetrate so deeply into the urothelium and into underlying layers. The aforementioned weight ratios also have a positive effect with regard to the stability of the composition according to the chemical buffer system.

Furthermore, concerning component (c) as used according to the invention, the composition can contain the dihydrogen phosphate/monohydrogen phosphate buffer system (component (c)) in a total concentration of dihydrogen phosphate/monohydrogen phosphate buffer system (component (c)) of (1.75±1.65) mg/ml, especially in a total concentration of (1.75±1.5) mg/ml, preferably in a total concentration of (1.75±1.25) mg/ml, by preference in a total concentration of (1.75±1) mg/ml, particularly preferably in a total concentration of (1.75±0.9) mg/ml, very particularly preferably in a total concentration of (1.75±0.8) mg/ml, yet further preferably in a total concentration of about 1.75 mg/ml.

In the context of the present invention, the specific use of a specific buffer system, especially chemical buffer system, as per component (c) based on the dihydrogen phosphate/monohydrogen phosphate buffer system has been found to be particularly advantageous. In the case of use of said specific buffer system, especially with simultaneous observance of the appropriate concentrations of the buffer or of the buffer components, there is significant counteracting of an undesired change in the pH and of an undesired degradation of the active ingredients during storage even over a relatively long period and there is thus significant improvement in the storability of the composition according to the invention, as stated above.

In particular, the composition can contain the dihydrogen phosphate/monohydrogen phosphate buffer system (component (c)) in a total amount of dihydrogen phosphate/monohydrogen phosphate buffer system (component (c)) of (87.5±85) mg, especially in a total amount of (87.5±75) mg, preferably in a total amount of (87.5±62.5) mg, by preference in a total amount of (87.5±50) mg, particularly preferably in a total amount of (87.5±45) mg, very particularly preferably in a total amount of (87.5±40) mg, yet further preferably in a total amount of about 87.5 mg.

Moreover, the composition can contain the dihydrogen phosphate of the dihydrogen phosphate/monohydrogen phosphate buffer system (component (c)), especially based on the weighed amount in producing and/or providing the composition, in a concentration of (0.2±0.19) mg/ml, especially in a concentration of (0.2±0.15) mg/ml, preferably in a concentration of (0.2±0.125) mg/ml, by preference in a concentration of (0.2±0.1) mg/ml, particularly preferably in a concentration of about 0.2 mg/ml.

Likewise, it has been found to be advantageous when the composition contains the monohydrogen phosphate of the dihydrogen phosphate/monohydrogen phosphate buffer system (component (c)), especially based on the weighed amount in producing and/or providing the composition, in a concentration of (1.5±1.4) mg/ml, especially in a concentration of (1.5±1.25) mg/ml, preferably in a concentration of (1.5±1.1) mg/ml, by preference in a concentration of (1.5±1) mg/ml, particularly preferably in a concentration of (1.5±0.75) mg/ml, very particularly preferably in a concentration of about 1.5 mg/ml.

With respect to the stabilization of the composition according to the invention, it has moreover been found to be particularly advantageous when the composition contains the dihydrogen phosphate/monohydrogen phosphate buffer system (component (c)) in a weight ratio (concentration ratio) of dihydrogen phosphate to monohydrogen phosphate [dihydrogen phosphate:monohydrogen phosphate], especially based on the weighed amount in producing and/or providing the composition, within the range from 2:1 to 1:100, preferably within the range from 1:1 to 1:75, by preference within the range from 1:2 to 1:50, particularly preferably within the range from 1:5 to 1:25.

In one embodiment according to the invention, the dihydrogen phosphate/monohydrogen phosphate buffer system (component (c)) can be present and/or configured as an alkali metal dihydrogen phosphate/alkali metal monohydrogen phosphate buffer system. Preferably, the alkali metal can be selected from sodium and/or potassium, especially sodium.

Moreover, the dihydrogen phosphate/monohydrogen phosphate buffer system (component (c)) can be present and/or configured as a sodium dihydrogen phosphate/sodium monohydrogen phosphate buffer system.

Furthermore, the dihydrogen phosphate/monohydrogen phosphate buffer system (component (c)) can be present and/or configured as a $NaH_2(PO_4)/Na_2H(PO_4)$ buffer system, especially as a $NaH_2(PO_4) \cdot 2\ H_2O/Na_2H(PO_4) \cdot 2\ H_2O$ buffer system.

In general, the dihydrogen phosphate/monohydrogen phosphate buffer system (component (c)) can serve and/or be used for setting and/or maintaining the pH of the composition. This results in a further stabilization of the composition according to the invention, associated with a particularly good compatibility of the composition according to the invention in the use or application thereof Phosphate buffers usable in the context of the present invention are generally commercially available, for example from Merck KGaA, Darmstadt (DE).

In relation to the term of buffer or chemical buffer system, reference can be made in particular to RÖMPP Lexikon Chemie [Römpp's Chemistry Lexicon], 10th edition, Georg-Thieme-Verlag, Stuttgart/New York, volume 5, 1998, pages 3618/3619, keyword: "buffer", and to the literature cited therein, the entire disclosure content of the aforementioned literature being hereby fully incorporated by reference.

In addition to the aforementioned ingredients and active substances, the composition according to the invention can comprise at least one physiologically compatible electrolyte as per component (d): In this connection, the composition can contain the electrolyte (component (d)) in a concentration of (8±6) mg/ml, especially in a concentration of (8±4) mg/ml, preferably in a concentration of (8±2) mg/ml, by preference in a concentration of (8±1) mg/ml, particularly preferably in a concentration of about 8 mg/ml.

In particular, the electrolyte (component (d)) can be present in the form of an alkali metal salt, especially in the form of an alkali metal chloride, preferably in the form of sodium chloride. According to the invention, it is preferred in this connection when the electrolyte (component (d)) is sodium chloride.

Electrolytes usable in the context of the present invention are generally commercially available, for example from Merck KGaA, Darmstadt (DE).

As a result of the use of an electrolyte, it is possible to minimize possible osmotic effects in the context of the application or treatment with the composition according to the invention, and this further increases the compatibility of the composition according to the invention.

In one embodiment preferred according to the invention, the present invention thus provides, according to the present aspect, also a composition, especially pharmaceutical composition, preferably for the prophylactic and/or therapeutic treatment of preferably inflammatory diseases of the urogenital tract, especially of inflammatory diseases of the bladder, preferably of cystitis, especially a composition described as above,
wherein the composition contains
(a) chondroitin sulfate sodium (sodium chondroitin sulfate) in a concentration of (20±2) mg/ml (component (a));
(b) sodium hyaluronate in a concentration of (16±1.6) mg/ml (component (b));
(c) an alkali metal dihydrogen phosphate/alkali metal monohydrogen phosphate buffer system (component (c)), especially in a total concentration of alkali metal dihydrogen phosphate/alkali metal monohydrogen phosphate buffer system of (1.75±1.65) mg/ml;
(d) at least one physiologically compatible electrolyte (component (d)), preferably sodium chloride, especially in a concentration of (8±6) mg/ml;
in combination and, in each case, in effective, especially pharmaceutically effective, amounts,
wherein the composition has a pH within the range from 6.1 to 7.9 and/or wherein the composition is set to a pH within the range from 6.1 to 7.9.

Concerning in general the pH of the composition according to the invention, the composition can moreover have a pH within the range from 6.6 to 7.7, especially within the range from 6.9 to 7.6, preferably within the range from 7.1 to 7.4. In particular, the pH of the composition can be maintained and/or set within the range from 6.6 to 7.7, especially within the range from 6.9 to 7.6, preferably within the range from 7.1 to 7.4. The pH can preferably be set and/or defined by means of the alkali metal dihydrogen phosphate/alkali metal monohydrogen phosphate buffer system (component (c)).

Observance of the aforementioned pH ranges significantly counteracts an undesired degradation of the active ingredients during storage even over a relatively long period and also significantly improves the storability of the composition according to the invention.

Owing to the aforementioned properties with respect to the pH, the composition according to the invention is moreover particularly highly compatible.

In the context of the present invention, pH determination can be carried out using methods known per se to a person skilled in the art. In particular, pH determination can be carried out on the basis of a potentiometric analysis. Preferably, pH determination can be carried out by the method according to Ph. Eur. [Pharmacopoea Europaea], 9th edition (9.0), 2017, 9th English edition, section 2.2.3. "Potentiometric determination of pH".

For further details in relation to the term of pH, reference can be made in particular to RÖMPP Lexikon Chemie [Römpp's Chemistry Lexicon], 10th edition, Georg-Thieme-Verlag, Stuttgart/New York, volume 4, 1998, pages 3230 to 3232, keyword: "pH", and to the literature cited therein, the entire disclosure content of the aforementioned literature being hereby fully incorporated by reference.

Further concerning the composition according to the invention, this can have a dynamic viscosity of at least 2000 mPas, especially at least 4000 mPas, preferably at least 5000 mPas, by preference at least 5250 mPas, at a temperature of 20° C. Moreover, the composition can have a dynamic viscosity of at most 7900 mPas, especially at most 6900 mPas, preferably at most 6000 mPas, by preference at most 5750 mPas, at a temperature of 20° C.

According to the invention, what can be provided in particular is that the composition has a dynamic viscosity within the range from 2000 mPas to 7900 mPas, especially within the range from 4000 mPas to 6900 mPas, preferably within the range from 5000 mPas to 6000 mPas, by preference within the range from 5250 mPas to 5750 mPas, at a temperature of 20° C.

The viscosity provided or set according to the invention ensures a particularly simple and less painful instillation of the composition into the bladder. Furthermore, owing to the viscosity provided according to the invention, there is a particularly good interaction of the active component underlying the composition according to the invention with the urothelium, and this has a positive effect on efficacy. Moreover, the specific setting of viscosity also leads to a further stabilization of the composition, especially with respect to—without wishing to be restricted or tied to this theory—the formation of a defined matrix or of a defined hydrogel, and this is associated with an improvement in the storage stability of the composition according to the invention.

Dynamic viscosity can be determined using methods known per se to a person skilled in the art. In particular, dynamic viscosity can be determined by the method according to Ph. Eur. [Pharmacopoea Europaea], 9th edition (9.0), 2017, 9th English edition, section 2.2.8. "Viscosity" and section 2.2.9. "Capillary viscometer method".

Furthermore, the composition according to the invention can have an osmolality within the range from 150 mosmol/kg to 600 mosmol/kg, especially within the range from 200 mosmol/kg to 550 mosmol/kg, preferably within the range from 250 mosmol/kg to 500 mosmol/kg, by preference within the range from 275 mosmol/kg to 450 mosmol/kg, particularly preferably within the range from 300 mosmol/kg to 400 mosmol/kg. The specific setting of osmolality likewise serves for the further stabilization and, in particular, improvement in compatibility of the composition according to the invention.

In this connection, osmolality can be determined by methods known per se to a person skilled in the art In particular, osmolality can be determined by the method according to Ph. Eur. [Pharmacopoea Europaea], 9th edition (9.0), 2017, 9th English edition, section 2.2.35. "Osmolality". Osmolality can, for example, also be set on the basis of the aforementioned electrolyte (component (d)), for example on the basis of alkali metal ions, such as sodium ions, and chloride ions, especially by means of sodium chloride.

Furthermore, the composition can have a density within the range from 1.001 g/cm$^3$ to 1.5 g/cm$^3$, especially within the range from 1.005 g/cm$^3$ to 1.25 g/cm$^3$, preferably within the range from 1.0075 g/cm$^3$ to 1.1 g/cm$^3$, by preference within the range from 1.0075 g/cm$^3$ to 1.075 g/cm$^3$, particularly preferably within the range from 1.0075 g/cm$^3$ to 1.05 g/cm$^3$, at a temperature of 20° C. and at a pressure of 1013.25 mbar (atmospheric pressure).

In particular, the composition can have a relative density, based on pure water, within the range from 1.001 to 1.5, especially within the range from 1.005 to 1.25, preferably within the range from 1.0075 to 1.1, by preference within the range from 1.0075 to 1.075, particularly preferably within the range from 1.0075 to 1.05, at a temperature of 20° C. and at a pressure of 1013.25 mbar (atmospheric pressure).

In the context of the present invention, density can be determined using methods known per se to a person skilled in the art. In particular, relative density can be determined by the method according to Ph. Eur. [Pharmacopoea Europaea], 9th edition (9.0), 2017, 9th English edition, section 2.2.5. "Relative density". Owing to the purposeful setting of density, it is possible to further improve the handling and compatibility of the composition according to the invention.

Furthermore, it is preferred in the context of the present invention when the composition is present as an aqueous composition. In this connection, what can be provided in particular is that the composition is aqueously based and/or is present as an aqueous formulation.

In particular, the composition can be present in the form of an aqueous solution and/or aqueous suspension, preferably in the form of an aqueous solution.

In this connection, the composition can contain water, especially purified water. In particular, the composition can contain water as pharmaceutically compatible carrier (excipient). In general, the composition can consequently be aqueously based, especially with use of water for injection purposes.

Concerning the amount of water that is used, this can vary within wide ranges. According to the invention, it is preferred when the composition according to the invention has a content of water, especially of purified water, of at least 50% by weight, especially at least 75% by weight, preferably at least 80% by weight, by preference at least 90% by weight, particularly preferably at least 95% by weight, based on the composition.

Water, especially water for injection purposes, that is usable in the context of the present invention is generally commercially available, for example from Fresenius Kabi Deutschland GmbH, Bad Homburg (DE).

In one embodiment according to the invention, what can be provided is that the composition according to the invention consists of the aforementioned components (a), (b), (c) and optionally (d) and also optionally water, especially purified water.

Furthermore, what can be provided according to the invention is that the composition according to the invention is at least substantially free of organic solvents and/or organic dispersants, especially alcohol-based solvents and/or alcohol-based dispersants. In particular, what can be provided according to the invention is that the composition is at least substantially free of alcohols. This further increases the compatibility of the composition according to the invention.

Not least because of the high stability, especially storage stability, of the composition according to the invention, what can also be provided in the context of the present invention is that the composition is at least substantially free of preservatives and/or at least substantially free of disinfectants. This also improves the compatibility of the composition according to the invention, since it is possible according to the invention to dispense with the use of additives that possibly have an irritant effect on the urothelium or the mucosa of the bladder.

As stated above, the present invention succeeds in providing a composition which is distinguished by an outstanding stability, with the result that the composition can be stored for long storage periods. Safety of use is also further increased on this basis.

In particular, the composition can be stable, especially storage-stable, for at least 6 months, especially at least 12 months, preferably at least 24 months, by preference at least 36 months, at temperatures within the range from 20° C. to 45° C., at a pressure of 1013.25 mbar (atmospheric pressure) and at a relative air humidity within the range from 50% to 90%. In this connection, the composition can have a total content of degradation products of components (a) and (b) of at most 5%, especially at most 4%, preferably at most 3%, by preference at most 2%, particularly preferably at most 1%, based on the total concentration of components (a) and (b) or of the educts, at the respective storage time point In particular, the composition can have a stability, especially storage stability, under accelerated aging conditions in accordance with ASTM F 1980 [ASTM F 1980: Standard Guide for Accelerated Aging of Sterile Barrier Systems for Medical Devices; 2007-04] at an aging temperature of 55° C. of at least 6 months, especially at least 12 months, preferably at least 24 months, by preference at least 36 months. In particular, the composition can, in this connection, have a total content of degradation products of components (a) and (b) of at most 5%, especially at most 4%, preferably at most 3%, by preference at most 2%, particularly preferably at most 1%, based on the total concentration of components (a) and (b) or of the educts, at the respective storage time point.

Furthermore, the composition according to the invention can be distinguished by a low content of alkaline earth metal constituents—if present at all.

In one embodiment according to the invention, the composition can have an alkaline earth metal salt concentration, especially calcium salt concentration and/or magnesium salt concentration, of at most 1 mg/ml, especially at most 0.5 mg/ml, preferably at most 0.1 mg/ml, by preference at most 0.05 mg/ml, particularly preferably at most 0.01 mg/ml.

In the context of the present invention, the composition can furthermore be at least substantially free of alkaline earth metal salts, especially at least substantially free of calcium salts and/or magnesium salts.

In general, the composition according to the invention can have an alkaline earth metal concentration, especially calcium concentration and/or magnesium concentration, of at most 1 mg/ml, especially at most 0.5 mg/ml, preferably at most 0.1 mg/ml, by preference at most 0.05 mg/ml, particularly preferably at most 0.01 mg/ml.

In particular, the composition according to the invention can be at least substantially free of alkaline earth metals, especially at least substantially free of calcium and/or magnesium salts.

Moreover, the composition can have a concentration of divalent ions, especially divalent cations, preferably alkaline earth metal ions, by preference calcium ions and/or magnesium ions, of at most 1 mg/ml, especially at most 0.5 mg/ml, preferably at most 0.1 mg/ml, by preference at most 0.05 mg/ml, particularly preferably at most 0.01 mg/ml.

In particular, the composition can be at least substantially free of divalent ions, especially divalent cations, preferably alkaline earth metal ions, by preference calcium ions and/or magnesium ions.

The concept of the invention that the composition according to the invention can be, according to the above remarks, at least substantially free of alkaline earth metal salts and/or alkaline earth metals, especially in ionic form, leads in particular to reduction or prevention of a relevant interaction with components (a) and/or (b) and/or (c), especially with respect to an avoidance of undesired complexation or the like. Consequently, it is possible on this basis to counteract a precipitation of active components and/or buffer components. In particular, it is possible on this basis to also avoid an undesired change in viscosity, especially as a result of an uncontrolled complexation or the like.

In one embodiment according to the invention, the composition can, especially in a form ready for use, ready for dosing and/or ready for application, be present at a volume of (50±10) ml, especially (50±5) ml, preferably (50±2) ml, by preference (50±1) ml, particularly preferably (50±0.5) ml, very particularly preferably about 50 ml.

In this connection, the composition can, especially in a form ready for use, ready for dosing and/or ready for application, be present and/or prepared for the administration, especially instillation into the bladder, of a volume of the composition of (50±10) ml, especially (50±5) ml, preferably (50±2) ml, by preference (50±1) ml, particularly preferably (50±0.5) ml, very particularly preferably about 50 ml. In particular, the composition can, especially in a form ready for use, ready for dosing and/or ready for application, be administered, especially by means of instillation into the bladder, at a volume of the composition of (50±10) ml, especially (50±5) ml, preferably (50±2) ml, by preference (50±1) ml, particularly preferably (50±0.5) ml, very particularly preferably about 50 ml.

Likewise, the composition can, especially in a form ready for use, ready for dosing and/or ready for application, be present with an active-ingredient amount of chondroitin sulfate and/or physiologically compatible chondroitin sulfate salt (component (a)) of (1000±100) mg, especially (1000±75) mg, preferably (1000±50) mg, by preference about 1000 mg.

Moreover, the composition according to the invention can, especially in a form ready for use, ready for dosing and/or ready for application, be present and/or prepared for the administration of an active-ingredient amount of chondroitin sulfate and/or physiologically compatible chondroitin sulfate salt (component (a)) of (1000±100) mg, especially (1000±75) mg, preferably (1000±50) mg, by preference about 1000 mg.

In this connection, the composition can, especially in a form ready for use, ready for dosing and/or ready for application, be administered at an active-ingredient amount of chondroitin sulfate and/or physiologically compatible chondroitin sulfate salt (component (a)) of (1000±100) mg, especially (1000±75) mg, preferably (1000±50) mg, by preference about 1000 mg.

Moreover, in this connection, the composition according to the invention can, especially in a form ready for use, ready for dosing and/or ready for application, be present with an active-ingredient amount of hyaluronic acid and/or physiologically compatible hyaluronic acid salt (hyaluronate) (component (b)) of (800±80) mg, especially (800±60) mg, preferably (800±40) mg, by preference about 800 mg.

According to the invention, the composition can, especially in a form ready for use, ready for dosing and/or ready for application, be present and/or prepared for the administration of an active-ingredient amount of hyaluronic acid and/or physiologically compatible hyaluronic acid salt (hyaluronate) (component (b)) of (800±80) mg, especially (800±60) mg, preferably (800±40) mg, by preference about 800 mg. In particular, the composition can, especially in a form ready for use, ready for dosing and/or ready for application, be administered at an active-ingredient amount of hyaluronic acid and/or physiologically compatible hyaluronic acid salt (hyaluronate) (component (b)) of (800±80) mg, especially (800±60) mg, preferably (800±40) mg, by preference about 800 mg.

The invention thus purposefully focuses especially on a high-dosage composition with respect to the active components (a) and (b), which moreover is preferably present in a form ready for use with a defined volume, as defined above. This is because the applicant has, in this connection, completely surprisingly found that the appropriately high and coordinated active-ingredient amounts with simultaneously high stability of the composition according to the invention lead to a particularly good efficacy with respect to the underlying diseases of the urogenital tract, especially cystitis, preferably interstitial cystitis, meaning that there is in this regard a stability and activity optimum. In this regard, the specific volume, as defined above, is also of great importance, since there is on this basis an optimal matching of the administration sizes of the composition to be applied or to be instilled to the pathological situation, especially in the case of cystitis, preferably interstitial cystitis, in that specifically there may often be a reduced bladder capacity or a so-called contracted bladder. Administration or instillation of the underlying specific volume can increase the holding time or holding period and thus how long the composition remains in the bladder, and this further improves the efficacy of the composition according to the invention.

In the context of the present invention, what can be provided in addition is that the composition is introduced and present in a storage and/or application device, especially in a storage and/or application container, specifically especially in a form ready for use, ready for dosing and/or ready for application.

In this connection, the composition can thus, especially in a form ready for use, ready for dosing and/or ready for application, be present in a storage and/or application device, especially in a storage and/or application container, preferably in volume sizes and/or with a volume of the composition of (50±10) ml, especially (50±5) ml, preferably (50±2) ml, by preference (50±1) ml, particularly preferably (50±0,5) ml, very particularly preferably about 50 ml, per container or application unit (dosing unit).

In particular, in this connection, the storage and/or application device according to the invention can be a preferably sterile syringe, especially application syringe, preferably disposable application syringe, especially with an accommodation volume or filling volume of (50±10) ml, especially (50±5) ml, preferably (50±2) ml, by preference (50±1) ml, particularly preferably (50±0.5) ml, very particularly preferably about 50 ml.

On the other hand, the storage and/or application device can also be present and/or configured in the form of a pierceable vial, preferably with a sterile closure, or the like.

According to the present aspect, the present invention also provides the composition according to the invention for instillation and/or for preferably topical application into the urogenital region, especially into the bladder.

In particular, the composition according to the invention can be prepared for administration and/or for instillation and/or for preferably topical application into the urogenital tract, especially into the bladder. Likewise, the composition according to the invention can, in this connection, be administered by means of instillation and/or by means of preferably topical application into the urogenital tract, especially into the bladder.

Likewise, the present invention also provides the composition according to the invention for use in the prophylactic and/or therapeutic treatment of preferably inflammatory diseases of the urogenital tract, especially of inflammatory diseases of the bladder, preferably of cystitis, especially acute or chronic cystitis, preferably interstitial cystitis, radiation cystitis, chronic recurrent cystitis, chemocystitis, chronic abacterial cystitis and chronic bacterial cystitis, particularly preferably interstitial cystitis.

Likewise, the present invention also provides the composition according to the invention for the prophylactic and/or therapeutic treatment of preferably inflammatory diseases of the urogenital tract, especially of inflammatory diseases of the bladder, preferably of cystitis, especially acute or chronic cystitis, preferably interstitial cystitis, radiation cystitis, chronic recurrent cystitis, chemocystitis, chronic abacterial cystitis and chronic bacterial cystitis, particularly preferably interstitial cystitis.

The present invention further provides—according to a further aspect of the present invention—also the use of the composition according to the invention, as defined above, for the prophylactic and/or therapeutic treatment of preferably inflammatory diseases of the urogenital tract, especially of inflammatory diseases of the bladder, preferably of cystitis, especially acute or chronic cystitis, preferably interstitial cystitis, radiation cystitis, chronic recurrent cystitis, chemocystitis, chronic abacterial cystitis and chronic bacterial cystitis, particularly preferably interstitial cystitis.

In this connection, the present invention likewise also provides the use of the composition according to the invention, as defined above, for the production of a drug or medicament for the prophylactic and/or therapeutic treatment of preferably inflammatory diseases of the urogenital tract, especially of inflammatory diseases of the bladder, preferably of cystitis, especially acute or chronic cystitis, preferably interstitial cystitis, radiation cystitis, chronic recurrent cystitis, chemocystitis, chronic abacterial cystitis and chronic bacterial cystitis, particularly preferably interstitial cystitis.

The composition according to the invention or combination containing, firstly, chondroitin sulfate and/or a physiologically compatible chondroitin sulfate salt (component (a)) and, secondly, hyaluronic acid and/or a physiologically compatible hyaluronic acid salt (component (b)) in a respectively specific concentration and furthermore a specific phosphate buffer system (component (c)) leads, in addition to the high stability, especially storage stability, that was surprisingly found, also to a particularly good efficacy with respect to the aforementioned diseases. A possible explanation for the outstanding action of the composition according to the invention can—without wishing to be restricted or tied to this theory—be seen in the active substances of the composition according to the invention interacting especially with the urothelium of the bladder in a particularly effective manner, there being in this regard an accumulation or embedding of the active substances on this layer, this leading to a repair of the glycosaminoglycan layer damaged by the disease and to a relevant regeneration. The reduction in the permeability of the urothelium that is associated with this mode of action—which to some extent amounts to a "sealing" effect with respect to the urine present in the bladder—leads to a distinct alleviation of the disease-related symptoms, especially also with respect to the underlying pain symptoms. Thus, the use of the composition according to the invention leads, just after a few treatments, to a significantly improved state of health in patients affected by the aforementioned diseases. The composition according to the invention can thus to some extent serve at least also for the temporary substitution of a defective glycosaminoglycan layer of the urothelium.

In this connection, the mode of action of the composition according to the invention—without wishing to be tied thereto—can be seen especially in a significantly physical interaction, in which the active ingredients as per component (a) and (b) are incorporated or embedded in the urothelium and/or accumulate thereon, with the result that a loss of chondroitin sulfate and/or hyaluronic acid, as caused by especially inflammatory reactions, in the bladder wall or in the urothelium is counterbalanced or compensated for. There is thus to some extent a regulation of the permeability or penetrability of the bladder wall, and this leads to a containment of the inflammatory reaction and thus to a supporting of wound healing and hence overall to an improvement in the state of health. The composition according to the invention forms virtually a shield of the bladder epithelium against irritating substances, such as bacteria, microcrystals or the like, the composition according to the invention acting as substitute and shield of the glycosaminoglycan layer in the bladder and in the discharging urinary tracts.

For the purposes of the uses according to the invention, the composition according to the invention can be instilled and/or topically applied into the urogenital region, especially into the bladder. In this process, the instillation and/or the application should be effected into the preferably prior emptied bladder. In this regard, the composition according to the invention can remain in the bladder for a period of several minutes up to a few hours for example in order to allow an optimal effect of the active ingredients on the urothelium. In this process, the highly concentrated composition provided according to the invention allows a particularly efficient interaction of the active ingredients in the form of components (a) and (b), present in high amounts or doses, with the urothelium, associated with a correspondingly high accumulation and/or embedding of the discussed active ingredients on and/or in the underlying layer of the bladder.

In this connection, the procedure can be carried out in particular such that the underlying volume of the composition present especially in the additionally below-described storage and/or application device is instilled into the bladder after complete emptying of the bladder, wherein the underlying volume should be especially about 50 ml. To achieve optimal results, the composition according to the invention should remain in the bladder for as long as possible, specificallY—as described above—for a period of several minutes up to several hours.

For example, in the context of the treatment of cystitis, the procedure can be to carry out the instillation of the composition according to the invention once a week for a period of four weeks, wherein the relevant individual dose of chondroitin sulfate or component (a) and the individual dose of hyaluronic acid or component (b) should be about 1000 mg and about 800 mg, respectively, in a volume of the composition of about 50 ml. In the context of a maintenance therapy, the composition according to the invention can subsequently be used, for example, once a month, especially until the symptoms have completely subsided. However, it is also possible to deviate from the aforementioned exemplary therapy scheme if necessary, depending on the particular case.

A further advantage of the inventive uses of the composition according to the invention can moreover be seen in said composition being safe with respect to its use and in no appreciable adverse effects occurring during the treatment, especially since the substances used are biocompatible substances. The particularly good compatibility is associated especially with the use of chondroitin sulfate of marine origin and/or hyaluronic acid of nonanimal origin.

The purposeful use of the aforementioned specific doses or amounts of active substances based on active components (a) and (b) moreover achieves a high efficacy of the composition according to the invention that is moreover not adversely affected by the specific phosphate buffer system. On the contrary, the specific use of the discussed buffer system as per component (c) in combination with the further measures according to the invention leads to an effective stabilization of the composition, and this leads to a high safety of use and high maintenance of efficacy or efficiency of action.

In summary, the composition according to the invention is preferably a medical device which, in one embodiment preferred according to the invention, contains a high-dosage solution or dispersion of the active ingredients based on components (a) and (b).

In general, the composition can be administered at least once a week, preferably over a period of preferably at least one month, by means of instillation and/or by means of topical application into the bladder.

Further concerning the composition according to the invention as such and the uses thereof, the composition can be administered and/or instilled and/or preferably topically applied into the bladder especially at least once a week, preferably over a period of preferably at least one month, and/or be prepared for at least weekly administration (at least once a week), preferably over a period of preferably at least one month, by means of instillation and/or topical application into the bladder, especially with a volume of the composition of (50±10) ml, especially (50±5) ml, preferably (50±2) ml, by preference (50±1) ml, particularly preferably (50±0.5) ml, very particularly preferably about 50 ml, and/or with an active-ingredient amount of chondroitin sulfate and/or physiologically compatible chondroitin sulfate salt (component (a)) of (1000±100) mg, especially (1000±75) mg, preferably (1000±50) mg, by preference about 1000 mg, and/or with an active-ingredient amount of hyaluronic acid and/or physiologically compatible hyaluronic acid salt (hyaluronate) (component (b)) of (800±80) mg, especially (800±60) mg, preferably (800±40) mg, by preference about 800 mg.

For further details in relation to the inventive uses of the composition according to the invention, reference can be made to the remarks relating to the other aspects of the invention, which apply mutatis mutandis with respect to the inventive uses.

The composition according to the invention is also distinguished in this connection by an outstanding storage stability and by a high efficiency of action with active-ingredient amounts optimized in this regard, as defined above.

According to an again further aspect of the present invention, the present invention likewise provides a storage and/or application device, especially a storage and/or application container, especially in the form of a preferably sterile syringe, especially application syringe, preferably disposable application syringe, preferably for instillation and/or for preferably topical application into the urogenital region, especially into the bladder, containing a composition according to the invention, as defined above.

In this connection, the present invention provides, according to this aspect, also a storage and/or application device, especially a storage and/or application container, especially in the form of a preferably sterile syringe, especially application syringe, preferably disposable application syringe, preferably for instillation and/or for preferably topical application into the urogenital region, especially into the bladder, containing a composition, especially as defined above, wherein the composition contains
- (a) chondroitin sulfate and/or a physiologically compatible chondroitin sulfate salt in an active-ingredient amount of (1000±100) mg (component (a));
- (b) hyaluronic acid and/or a physiologically compatible hyaluronic acid salt (hyaluronate) in an active-ingredient amount of (800±80) mg (component (b));
- (c) a dihydrogen phosphate/monohydrogen phosphate buffer system (component (c));
- (d) optionally at least one physiologically compatible electrolyte (component (d));

in combination and, in each case, in effective, especially pharmaceutically effective, amounts,
wherein the composition has a pH within the range from 6.1 to 7.9 and/or wherein the composition is set to a pH within the range from 6.1 to 7.9.

According to the invention, it is preferred in this connection when the storage and/or application device has an accommodation volume or filling volume of (50±10) ml, especially (50±5) ml, preferably (50±2) ml, by preference (50±1) ml, particularly preferably (50±0.5) ml, very particularly preferably about 50 ml.

In particular, the composition can have an active-ingredient amount of (a) chondroitin sulfate and/or physiologically compatible chondroitin sulfate salt (component (a)) of (1000±75) mg, preferably (1000±50) mg, by preference about 1000 mg.

Moreover, the composition can have an active-ingredient amount of (b) hyaluronic acid and/or physiologically compatible hyaluronic acid salt (hyaluronate) (component (b)) of (800±60) mg, preferably (800±40) mg, by preference about 800 mg.

According to the invention, what can moreover be provided is that the composition comprises the dihydrogen phosphate/monohydrogen phosphate buffer system (component (c)) in a total amount of dihydrogen phosphate/monohydrogen phosphate buffer system (component (c)) of (87.5±85) mg, especially in a total amount of (87.5±75) mg, preferably in a total amount of (87.5±62.5) mg, by preference in a total amount of (87.5±50) mg, particularly preferably in a total amount of (87.5±45) mg, very particularly preferably in a total amount of (87.5±40) mg, yet further preferably in a total amount of about 87.5 mg.

In particular, the composition can contain the electrolyte (component (d)) in an amount of (400±300) mg, especially in an amount of (400±200) mg, preferably in an amount of (400±100) mg, by preference in an amount of (400±50) mg, particularly preferably in an amount of about 400 mg.

According to the invention, what can moreover be provided is that the chondroitin sulfate and/or the physiologically compatible chondroitin sulfate salt (component (a)) is present in the form of an alkali metal salt, preferably in the form of a sodium salt Likewise, what can be provided according to the invention is that the chondroitin sulfate and/or the physiologically compatible chondroitin sulfate salt (component (a)) is present in the form of chondroitin sulfate sodium (sodium chondroitin sulfate).

Moreover, the hyaluronic acid and/or the physiologically compatible hyaluronic acid salt (component (b)) can be present in the form of an alkali metal salt, preferably in the form of a sodium salt, and/or in the form of an alkali metal hyaluronate.

In particular, the hyaluronic acid and/or the physiologically compatible hyaluronic acid salt (component (b)) can be present in the form of sodium hyaluronate.

Furthermore, the dihydrogen phosphate/monohydrogen phosphate buffer system (component (c)) can be present and/or configured as an alkali metal dihydrogen phosphate/alkali metal monohydrogen phosphate buffer system. In this connection, the alkali metal can be selected from sodium and/or potassium, especially sodium.

In particular, the dihydrogen phosphate/monohydrogen phosphate buffer system (component (c)) can be present and/or configured as a sodium dihydrogen phosphate/sodium monohydrogen phosphate buffer system.

Furthermore, the electrolyte (component (d)) can be present and/or configured in the form of an alkali metal salt, especially in the form of an alkali metal chloride, preferably in the form of sodium chloride. In particular, the electrolyte (component (d)) can be sodium chloride.

Further concerning the composition, it can have a pH within the range from 6.6 to 7.7, especially within the range from 6.9 to 7.6, preferably within the range from 7.1 to 7.4.

In particular, the pH of the composition can be maintained and/or set within the range from 6.6 to 7.7, especially within the range from 6.9 to 7.6, preferably within the range from 7.1 to 7.4. The pH can preferably be set and/or defined by means of the alkali metal dihydrogen phosphate/alkali metal monohydrogen phosphate buffer system (component (c)).

In particular, the composition can have a dynamic viscosity of at least 2000 mPas, especially at least 4000 mPas, preferably at least 5000 mPas, by preference at least 5250 mPas, at a temperature of 20° C.

Likewise, the composition can have a dynamic viscosity of at most 7900 mPas, especially at most 6900 mPas, preferably at most 6000 mPas, by preference at most 5750 mPas, at a temperature of 20° C.

Moreover, the composition can have a dynamic viscosity within the range from 2000 mPas to 7900 mPas, especially within the range from 4000 mPas to 6900 mPas, preferably within the range from 5000 mPas to 6000 mPas, by preference within the range from 5250 mPas to 5750 mPas, at a temperature of 20° C.

Furthermore, the composition can have an osmolality within the range from 150 mosmol/kg to 600 mosmol/kg, especially within the range from 200 mosmol/kg to 550 mosmol/kg, preferably within the range from 250 mosmol/kg to 500 mosmol/kg, by preference within the range from 275 mosmol/kg to 450 mosmol/kg, particularly preferably within the range from 300 mosmol/kg to 400 mosmol/kg.

Furthermore, the composition can have a density within the range from 1.001 g/cm$^3$ to 1.5 g/cm$^3$, especially within the range from 1.005 g/cm$^3$ to 1.25 g/cm$^3$, preferably within the range from 1.0075 g/cm$^3$ to 1.1 g/cm$^3$, by preference within the range from 1.0075 g/cm$^3$ to 1.075 g/cm$^3$, particularly preferably within the range from 1.0075 g/cm$^3$ to 1.05 g/cm$^3$, at a temperature of 20° C. and at a pressure of 1013.25 mbar (atmospheric pressure).

In particular, the composition can have a relative density, based on pure water, within the range from 1.001 to 1.5, especially within the range from 1.005 to 1.25, preferably within the range from 1.0075 to 1.1, by preference within the range from 1.0075 to 1.075, particularly preferably within the range from 1.0075 to 1.05, at a temperature of 20° C. and at a pressure of 1013.25 mbar (atmospheric pressure).

According to the invention, it is preferred when the storage and/or application device contains the composition, especially in a form ready for use, ready for dosing and/or ready for application, at a volume of (50±10) ml, especially (50±5) ml, preferably (50±2) ml, by preference (50±1) ml, particularly preferably (50±0.5) ml, very particularly preferably about 50 ml.

In particular, the composition can be present at a volume of (50±10) ml, especially (50±5) ml, preferably (50±2) ml, by preference (50±1) ml, particularly preferably (50±0.5) ml, very particularly preferably about 50 ml.

According to the invention, it is moreover preferred when the composition is present as an aqueous composition. In particular, the composition can be especially aqueously based and/or be present as an aqueous formulation, especially in the form of an aqueous solution and/or aqueous suspension, preferably in the form of an aqueous solution.

In particular, the composition can contain water, especially purified water. In particular, the composition can contain water as pharmaceutically compatible carrier (excipient). According to the invention, the composition can, then, be aqueously based. In this connection, the composition can have a content of water of at least 50% by weight, especially at least 75% by weight, preferably at least 80% by weight, by preference at least 90% by weight, particularly preferably at least 95% by weight, based on the composition.

According to the invention, the composition according to the invention that is provided for the storage and/or application device can consist of the aforementioned components (a), (b), (c) and optionally (d) and also water.

For further details in relation to the inventive storage and/or application device containing the composition according to the invention, reference can moreover be made to the embodiments relating to the other aspects of the invention, which apply mutatis mutandis with respect to the inventive storage and/or application device.

Furthermore, the present invention provides—according to an again further aspect of the present invention—also the package unit according to the invention, which contains at least one storage and/or application device, as defined above. In this connection, the storage and/or application device can be present in outer packaging protecting against contamination. For further details in relation to the package unit according to the invention, reference can be made to the remarks relating to the other aspects of the invention, which apply mutatis mutandis with respect to the package unit according to the invention.

Lastly, the present invention provides—according to a further aspect of the present invention—also the kit according to the invention, especially instillation system, comprising (i) at least one storage and/or application device, as defined above, and (ii) at least one composition, as defined above, especially wherein the composition is present in the storage and/or application device preferably in a form ready for use, ready for dosing and/or ready for application, and (iii) at least one instillation device connectable to the storage and/or application device, especially in the form of an instillation hose or the like.

The kit according to the invention provides in particular an appropriate installation system with simple handleability, rapid readiness for use, and high safety of use.

For further details in relation to the kit according to the invention, reference can be made to the preceding remarks relating to the other aspects of the invention, which apply mutatis mutandis with respect to the kit according to the invention.

On the basis of the inventive composition with the high-dosage active-ingredient components, the present invention thus provides altogether an effective overall concept for the treatment of preferably inflammatory diseases of the urogenital tract, such as of cystitis, preferably interstitial cystitis, the inventive composition having not only a high efficacy with respect to the underlying disease with, at the same time, low adverse effects and outstanding handleability, but also a significantly increased stability, especially storage stability.

Further configurations, modifications and variations and also advantages of the present invention are readily identifiable and realizable for a person skilled in the art upon reading the description, without said person departing from the scope of the present invention while doing so.

The following exemplary embodiments serve merely to illustrate the present invention, but without restricting the present invention thereto.

Exemplary Embodiments

1. Preparation Examples

A procedure known per se to a person skilled in the art is used to prepare 50 ml in each case of a clear, possibly slightly yellow-colored aqueous solution of compositions according to the invention.

First of all, a defined subamount (especially about 75% of the desired final volume) of purified water is initially charged at room temperature and ambient pressure in a glass vessel having a stirrer. While stirring, first an electrolyte in the form of sodium chloride and then the buffer system component in the form of sodium dihydrogen phosphate and disodium hydrogen phosphate are added. After complete dissolution of the components, the pH is determined and is set to the desired value (e.g., pH of approx. 7), using phosphoric acid or sodium hydroxide solution if necessary.

Thereafter, the amounts and types of the further ingredients and active ingredients, as specified below in the formulation examples, are added while stirring, specifically component (a) in the form of chondroitin sulfate salt (chondroitin sulfate sodium) and component (b) in the form of sodium hyaluronate. The solution is topped up with further water to the desired final volume of 50 ml.

Thereafter, the pH of the composition obtained is determined again and readjusted if necessary. The remaining relevant specifications of the solutions are checked, too, for the value ranges set or prechosen (e.g., osmolality; relative density; microbiological purity and sterility; exclusion of impurities, especially degradation products of the ingredients and active ingredients; viscosity; appearance).

The solution thus obtained can subsequently be subjected to a sterile filtration, for example with the aid of nitrogen across a filter cartridge with a specific filter system, and then filled into an especially sterile accommodation and/or application container, such as a plastic syringe or the like. The composition obtained can be used for further stability tests or for relevant use and/or efficacy tests.

In accordance with these general preparation instructions, the formulations or compositions specified below are prepared by dissolution in water of the following components at the relevant specified amounts (weighed amount for preparation of composition):

Composition A1 (specified value per 50 ml of composition)

| Ingredient | Amount/mg | Quality |
|---|---|---|
| Chondroitin sulfate sodium $M_n$ = 15 kDa; $M_w$ = 100 kDa; $M_z$ = 430 kDa | 1000 | Ph. Eur. |
| Sodium hyaluronate $M_n$ = 55 kDa; $M_w$ = 200 kDa; $M_z$ = 700 kDa | 800 | Ph. Eur. |
| Buffer system: | | Ph. Eur. |
| sodium dihydrogen phosphate ($NaH_2(PO_4) \cdot 2\ H_2O$)/ | 11 | |
| disodium hydrogen phosphate ($Na_2H(PO_4) \cdot 2\ H_2O$) | 76 | |
| Electrolyte (sodium chloride) | 395 | Ph. Eur. |
| Purified water | to 50 ml | Ph. Eur. |

The pH of composition A1 is moreover about 7.2. Furthermore, the present composition has a dynamic viscosity of about 5600 mPas, and the density is about 1.022 g/cm³ (20° C. and atmospheric pressure). The osmolality of the present composition is moreover about 370 mosmol/kg.

Compositions B1 to B4

Further compositions in line with composition A1 are prepared, but with the proviso that different amounts of chondroitin sulfate sodium are used:

| Composition | Amount of chondroitin sulfate sodium/mg |
|---|---|
| Composition B1 | 850 |
| Composition B2 | 900 |
| Composition B3 | 1100 |
| Composition B4 | 1150 |

Compositions B5 to B8

Further compositions in line with composition A1 are again prepared, but with the proviso that different amounts of sodium hyaluronate are used:

| Composition | Amount of sodium hyaluronate/mg |
|---|---|
| Composition B5 | 720 |
| Composition B6 | 680 |
| Composition B7 | 880 |
| Composition B8 | 940 |

Compositions C1 and C2

Further compositions in line with composition A1 are again prepared, but with the proviso that the chondroitin sulfate sodium (CS—Na) is used with different molar masses at an amount used in this connection of 1000 mg in each case:

| Composition | CS-Na $M_n$ | CS-Na $M_w$ | CS-Na $M_z$ |
|---|---|---|---|
| Composition C1 | 1 kDa | 5 kDa | 50 kDa |
| Composition C2 | 35 kDa | 250 kDa | 1100 kDa |

Compositions D1 and D2

Again further compositions are in line with composition A1, but with the proviso that the sodium hyaluronate (HA-Na) is used with different molar masses at an amount used in this connection of 800 mg in each case:

| Composition | HA-Na $M_n$ | HA-Na $M_w$ | HA-Na $M_z$ |
|---|---|---|---|
| Composition D1 | 2 kDa | 4 kDa | 275 kDa |
| Composition D2 | 275 kDa | 325 kDa | 1750 kDa |

Compositions E1 to E4

For again further compositions based on composition A1, the pH is varied as shown below:

| Composition | pH |
|---|---|
| Composition E1 | 5.5 |
| Composition E2 | 6.1 |
| Composition E3 | 7.9 |
| Composition E4 | 8.5 |

Compositions F1 to F4

For again further compositions, the buffer system is varied; to this end, amounts correlating to the phosphate buffer system used in composition A1 are used of buffer systems based on carbonic acid/bicarbonate, acetic acid/acetate, carbonic acid/silicate and citric acid/citrate; compositions F1 to F4 are thus in line with composition A1, with the proviso that a different buffer system is used in this connection (comparison):

| Composition | Buffer system |
|---|---|
| Composition F1 | Carbonic acid/bicarbonate |
| Composition F2 | Acetic acid/acetate |
| Composition F3 | Carbonic acid/silicate |
| Composition F4 | Citric acid/citrate |

2. Stability Tests

Stability tests are carried out on respective batches of the composition as per the formulations described above.

For this purpose, firstly, the total content of degradation products of the components used in the stated compositions is determined at appropriate storage times or storage time points, specifically at the start of the tests and at appropriate storage times of 3 months, 6 months, 12 months, 18 months, 24 months, 36 months and 39 months in each case. Secondly, pH and viscosity are also determined over the same storage period at the aforementioned storage times.

Here, a first batch of the compositions is stored at a temperature of (25±2) ° C. and at a relative ambient air humidity of (60±5) % r. h. (Tables 1A to 1F below).

Moreover, a further batch of the compositions is stored at a temperature of (40±2) ° C. and at a relative ambient air humidity of (75±5) % r. h. (Tables 2A to 2F below).

Tables 1A to 1F and 2A to 2F below show the results ascertained in this connection. In the tables below, "++" means a total content of degradation products ("Degrad.") at the respective storage time point of at most 3%, based on the total concentration of the components, or a change in pH ("pH") or in viscosity ("Visco.") at the respective storage time point of at most 3%, based on the respective starting value. Furthermore, "+" means a total content of degradation products at the respective storage time point of at most 5%, based on the total concentration of the components, or a change in pH or in viscosity at the respective storage time point of at most 5%, based on the respective starting value. Lastly, "−" means a total content of degradation products at the respective storage time point of more than 5%, based on the total concentration of the components, or a change in pH or in viscosity at the respective storage time point of more than 5%, based on the respective starting value.

TABLE 1A

[(25 ± 2) ° C. and (60 ± 5) % r.h.]:

| | | 3 M | 6 M | 12 M | 18 M | 24 M | 36 M | 39 M |
|---|---|---|---|---|---|---|---|---|
| A1 | Degrad. | ++ | ++ | ++ | ++ | ++ | ++ | ++ |
|  | pH | ++ | ++ | ++ | ++ | ++ | ++ | ++ |
|  | Visco. | ++ | ++ | ++ | ++ | ++ | ++ | ++ |

TABLE 1B

[(25 ± 2) ° C. and (60 ± 5) % r.h.]:

| | | 3 M | 6 M | 12 M | 18 M | 24 M | 36 M | 39 M |
|---|---|---|---|---|---|---|---|---|
| B1 | Degrad. | ++ | ++ | ++ | + | + | + | + |
|  | pH | ++ | ++ | ++ | ++ | + | + | + |
|  | Visco. | ++ | ++ | ++ | ++ | + | + | + |
| B2 | Degrad. | ++ | ++ | ++ | ++ | ++ | ++ | + |
|  | pH | ++ | ++ | ++ | ++ | ++ | ++ | + |
|  | Visco. | ++ | ++ | ++ | ++ | ++ | + | + |
| B3 | Degrad. | ++ | ++ | ++ | ++ | ++ | ++ | + |
|  | pH | ++ | ++ | ++ | ++ | ++ | ++ | + |
|  | Visco. | ++ | ++ | ++ | ++ | + | + | + |
| B4 | Degrad. | ++ | ++ | ++ | + | + | + | + |
|  | pH | ++ | ++ | ++ | + | + | + | + |
|  | Visco. | ++ | ++ | ++ | + | + | + | + |
| B5 | Degrad. | ++ | ++ | ++ | + | + | + | + |
|  | pH | ++ | ++ | ++ | + | + | + | + |
|  | Visco. | ++ | ++ | ++ | + | + | + | + |
| B6 | Degrad. | ++ | ++ | ++ | ++ | + | + | + |
|  | pH | ++ | ++ | ++ | ++ | ++ | + | + |
|  | Visco. | ++ | ++ | ++ | ++ | ++ | + | + |
| B7 | Degrad. | ++ | ++ | ++ | ++ | + | + | + |
|  | pH | ++ | ++ | ++ | ++ | ++ | ++ | + |
|  | Visco. | ++ | ++ | ++ | + | + | + | + |
| B8 | Degrad. | ++ | ++ | ++ | + | + | + | + |
|  | pH | ++ | ++ | ++ | + | + | + | + |
|  | Visco. | ++ | ++ | + | + | + | + | + |

TABLE 1C

[(25 ± 2) ° C. and (60 ± 5) % r.h.]:

| | | 3 M | 6 M | 12 M | 18 M | 24 M | 36 M | 39 M |
|---|---|---|---|---|---|---|---|---|
| C1 | Degrad. | ++ | ++ | ++ | + | + | + | + |
|  | pH | ++ | ++ | ++ | + | + | + | + |
|  | Visco. | ++ | ++ | + | + | + | + | + |
| C2 | Degrad. | ++ | ++ | ++ | + | + | + | + |
|  | pH | ++ | ++ | ++ | ++ | + | + | + |
|  | Visco. | ++ | ++ | ++ | ++ | + | + | + |

TABLE 1D

[(25 ± 2) ° C. and (60 ± 5) % r.h.]:

|    |        | 3 M | 6 M | 12 M | 18 M | 24 M | 36 M | 39 M |
|----|--------|-----|-----|------|------|------|------|------|
| D1 | Degrad.| ++  | ++  | ++   | +    | +    | +    | +    |
|    | pH     | ++  | ++  | ++   | +    | +    | +    | +    |
|    | Visco. | ++  | ++  | +    | +    | +    | +    | +    |
| D2 | Degrad.| ++  | ++  | +    | +    | +    | +    | +    |
|    | pH     | ++  | ++  | ++   | +    | +    | +    | +    |
|    | Visco. | ++  | ++  | ++   | +    | +    | +    | +    |

TABLE 1E

[(25 ± 2) ° C. and (60 ± 5) % r.h.]:

|    |        | 3 M | 6 M | 12 M | 18 M | 24 M | 36 M | 39 M |
|----|--------|-----|-----|------|------|------|------|------|
| E1 | Degrad.| ++  | ++  | +    | +    | +    | −    | −    |
|    | pH     | ++  | ++  | +    | +    | +    | +    | −    |
|    | Visco. | ++  | ++  | +    | +    | +    | −    | −    |
| E2 | Degrad.| ++  | ++  | ++   | ++   | ++   | +    | +    |
|    | pH     | ++  | ++  | ++   | ++   | ++   | +    | +    |
|    | Visco. | ++  | ++  | ++   | ++   | ++   | +    | +    |
| E3 | Degrad.| ++  | ++  | ++   | ++   | ++   | +    | +    |
|    | pH     | ++  | ++  | ++   | ++   | ++   | +    | +    |
|    | Visco. | ++  | ++  | ++   | ++   | +    | +    | +    |
| E4 | Degrad.| ++  | ++  | +    | +    | +    | −    | −    |
|    | pH     | ++  | ++  | ++   | +    | +    | +    | −    |
|    | Visco. | ++  | ++  | +    | +    | +    | +    | −    |

TABLE 1F

[(25 ± 2) ° C. and (60 ± 5) % r.h.]:

|    |        | 3 M | 6 M | 12 M | 18 M | 24 M | 36 M | 39 M |
|----|--------|-----|-----|------|------|------|------|------|
| F1 | Degrad.| ++  | ++  | +    | −    | −    | −    | −    |
|    | pH     | ++  | ++  | +    | +    | +    | −    | −    |
|    | Visco. | ++  | ++  | +    | +    | −    | −    | −    |
| F2 | Degrad.| ++  | ++  | +    | +    | −    | −    | −    |
|    | pH     | ++  | ++  | +    | +    | +    | −    | −    |
|    | Visco. | ++  | ++  | +    | +    | +    | −    | −    |
| F3 | Degrad.| ++  | ++  | +    | +    | −    | −    | −    |
|    | pH     | ++  | ++  | +    | +    | +    | −    | −    |
|    | Visco. | ++  | ++  | +    | +    | +    | −    | −    |
| F4 | Degrad.| ++  | ++  | +    | +    | +    | −    | −    |
|    | pH     | ++  | ++  | +    | +    | +    | −    | −    |
|    | Visco. | ++  | ++  | +    | +    | +    | −    | −    |

TABLE 2A

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| A1 | Degrad.| ++  | ++  | ++   | ++   | ++   | +    | +    |
|    | pH     | ++  | ++  | ++   | ++   | +    | +    | +    |
|    | Visco. | ++  | ++  | ++   | ++   | ++   | +    | +    |

TABLE 2B

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| B1 | Degrad.| ++  | ++  | ++   | +    | +    | +    | −    |
|    | pH     | ++  | ++  | +    | +    | +    | +    | +    |
|    | Visco. | ++  | ++  | +    | +    | +    | +    | +    |
| B2 | Degrad.| ++  | ++  | ++   | ++   | +    | +    | −    |
|    | pH     | ++  | ++  | ++   | ++   | +    | +    | +    |
|    | Visco. | ++  | ++  | ++   | +    | +    | +    | +    |

TABLE 2B-continued

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| B3 | Degrad.| ++  | ++  | ++   | +    | +    | +    | +    |
|    | pH     | ++  | ++  | ++   | +    | +    | +    | +    |
|    | Visco. | ++  | ++  | +    | +    | +    | +    | +    |
| B4 | Degrad.| ++  | ++  | +    | +    | +    | −    | −    |
|    | pH     | ++  | ++  | +    | ++   | +    | +    | −    |
|    | Visco. | ++  | +   | +    | +    | +    | −    | −    |
| B5 | Degrad.| ++  | ++  | ++   | +    | +    | +    | −    |
|    | pH     | ++  | ++  | ++   | +    | +    | +    | −    |
|    | Visco. | ++  | ++  | ++   | +    | +    | +    | −    |
| B6 | Degrad.| ++  | ++  | ++   | ++   | ++   | +    | +    |
|    | pH     | ++  | ++  | ++   | ++   | ++   | +    | −    |
|    | Visco. | ++  | ++  | ++   | ++   | ++   | +    | −    |
| B7 | Degrad.| ++  | ++  | ++   | ++   | +    | +    | −    |
|    | pH     | ++  | ++  | ++   | ++   | +    | +    | −    |
|    | Visco. | ++  | ++  | ++   | +    | +    | −    | −    |
| B8 | Degrad.| ++  | +   | +    | +    | −    | −    | −    |
|    | pH     | ++  | ++  | +    | +    | +    | −    | −    |
|    | Visco. | ++  | ++  | ++   | +    | +    | −    | −    |

TABLE 2C

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| C1 | Degrad.| ++  | ++  | ++   | +    | +    | +    | +    |
|    | pH     | ++  | ++  | +    | +    | +    | +    | −    |
|    | Visco. | ++  | +   | +    | +    | +    | +    | −    |
| C2 | Degrad.| ++  | ++  | +    | +    | +    | −    | −    |
|    | pH     | ++  | ++  | ++   | +    | +    | +    | −    |
|    | Visco. | ++  | ++  | +    | +    | +    | −    | −    |

TABLE 2D

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| D1 | Degrad.| ++  | ++  | +    | +    | +    | +    | −    |
|    | pH     | ++  | ++  | +    | +    | +    | +    | +    |
|    | Visco. | ++  | +   | +    | +    | +    | +    | −    |
| D2 | Degrad.| ++  | ++  | +    | +    | +    | +    | −    |
|    | pH     | ++  | ++  | +    | +    | +    | +    | +    |
|    | Visco. | ++  | +   | +    | +    | −    | −    | −    |

TABLE 2E

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| E1 | Degrad.| +   | +   | +    | +    | −    | −    | −    |
|    | pH     | ++  | +   | +    | +    | −    | −    | −    |
|    | Visco. | ++  | +   | +    | +    | −    | −    | −    |
| E2 | Degrad.| ++  | ++  | ++   | +    | +    | +    | −    |
|    | pH     | ++  | ++  | ++   | +    | +    | +    | −    |
|    | Visco. | ++  | ++  | ++   | +    | +    | −    | −    |
| E3 | Degrad.| ++  | ++  | ++   | +    | +    | +    | −    |
|    | pH     | ++  | ++  | ++   | +    | +    | +    | +    |
|    | Visco. | ++  | ++  | ++   | +    | +    | +    | −    |
| E4 | Degrad.| ++  | +   | +    | +    | −    | −    | −    |
|    | pH     | ++  | ++  | +    | +    | +    | −    | −    |
|    | Visco. | ++  | +   | +    | +    | +    | −    | −    |

TABLE 2F

[(40 ± 2) ° C. and (75 ± 5) % r.h.]:

|    |        | 3 M | 6 M | 12 M | 18 M | 24 M | 36 M | 39 M |
|----|--------|-----|-----|------|------|------|------|------|
| F1 | Degrad.| ++  | +   | −    | −    | −    | −    | −    |
|    | pH     | ++  | +   | +    | −    | −    | −    | −    |
|    | Visco. | ++  | +   | +    | −    | −    | −    | −    |
| F2 | Degrad.| ++  | +   | +    | −    | −    | −    | −    |
|    | pH     | ++  | +   | +    | +    | −    | −    | −    |
|    | Visco. | ++  | +   | +    | +    | −    | −    | −    |
| F3 | Degrad.| +   | −   | −    | −    | −    | −    | −    |
|    | pH     | ++  | +   | −    | −    | −    | −    | −    |
|    | Visco. | +   | +   | −    | −    | −    | −    | −    |
| F4 | Degrad.| ++  | +   | +    | −    | −    | −    | −    |
|    | pH     | ++  | ++  | +    | +    | −    | −    | −    |
|    | Visco. | ++  | +   | +    | −    | −    | −    | −    |

One characteristic measure of the stability of a composition is, firstly, the constancy of the pH and of the viscosity and also the constancy of the content of active ingredients (i.e., component (a) and component (b)). Furthermore, it is possible to determine the content of degradation products in the composition to assess the stability of the composition.

Against this background, the stability tests carried out show that both the amount of active-ingredient components in the composition and the specific molecular weight thereof, and additionally also the pH and significantly also the buffer system used, exert a significant influence on the stability, especially storage stability, of the underlying compositions, with composition A1, which has the specific harmonization of the components, exhibiting the best properties in this connection.

Moreover, the tests with use of different buffer systems show that, significantly, a reliable long-term stability can only be achieved with the phosphate buffer system used according to the invention. This is because, as surprisingly shown by the applicant's stability tests, only such a phosphate buffer system—compared to other possible usable buffer systems—brings about the striven-for and reliable long-term stabilization of the composition according to the invention even over long periods. By contrast, with other buffer systems which can be used within the comparable pH range, such as, for example, a carbonic acid/bicarbonate buffer system, a carbonic acid/silicate buffer system, an acetic acid/acetate buffer system, a citric acid/citrate buffer system or the like, such good stability results cannot be obtained or cannot always be reliably obtained. Without wishing to be tied to a particular theory, this effect of the phosphate buffer system used according to the invention may possibly also be attributed to secondary effects, for example with respect to a further stabilization of the matrix or the hydrogel based on components (a) and (b) in the composition.

As demonstrated by the above-stated results of the applicant's stability tests, intensive research effort by the applicant was required to find a stable composition for the treatment of preferably inflammatory diseases of the urogenital tract, especially of inflammatory diseases of the bladder, preferably of cystitis, of the kind of the present invention.

Furthermore, the above stability tests also show the complexity of the approach to achieving the object of the present invention found by the applicant. This includes the joint presence of the active ingredients or components (a) and (b) in defined amounts with simultaneous observance or maintenance of the pH of the composition within the above-defined range—and also further factors, such as the selection of the suitable buffer system.

Surprisingly, the approach according to the invention ultimately manages with only a few additional ingredients, which, however, do not affect the pharmacological efficacy of the underlying active ingredients; this is of crucial importance with respect to the intended pharmaceutical action.

The results demonstrate not least as a whole the excellent long-term stability of the composition according to the invention.

3. Usage Observations and Efficacy Studies

Over a period of two months, respective groups of test subjects with a diagnosed interstitial (i.e., nonbacterial) cystitis are administered with the above-stated compositions A1 and B1, B4 (amount of chondroitin sulfate sodium); B5, B8 (amount of sodium hyaluronate); C1, C2 (molar mass of chondroitin sulfate sodium); D1, D2 (molar mass of sodium hyaluronate) and also E1 and E4 (pH). The administration is carried out by means of instillation into the bladder. The administration is repeated in each case every week over a period of two months. The volume of the instilled composition is 50 ml in each case. 10 test subjects are tested per approach or composition. The test intervals are in each case 1 week, 2 weeks, 1 month and lastly 2 months, based in each case on the day of the first instillation. In this process, the following test sets are carried out:

a) In the context of the first test set, the test subjects indicate their subjective feeling on the basis of a school grades scale from 1 to 6 (1=very good to 6=unsatisfactory), with any intermediate values also being possible. In this test, the focus is especially on pain in the region of the bladder and of the pelvis, excessive urinary urgency and on a small bladder capacity. The respective mean values and the associated standard deviations are ascertained.

b) In a second test, a cytoscopy is carried out one month after the first application of the aforementioned compositions in the respective test-subject groups, with use of an endoscope for a visual assessment of the bladder urothelium.

c) Furthermore, urine samples are collected at the start of the test and after one month, and the content of glycosaminoglycan in the urine is ascertained in accordance with the method by Whitley et al. (cf. C. B., Ridnour, M. D., Draper, K A., Dutton, C. M. and Negila, J. P.: Diagnostic test for mucopolysaccharidosis. I. Direct method for quantifying excessive urinary glycosaminoglycan excretion. Clin. Chem., 35: 374, 1989), involving staining of the glycosaminoglycans present in the urine using dimethylmethylene blue and subsequently determining the concentrations thereof by means of spec-troscopy. In this connection, it is known that, in patients with diagnosed interstitial cystitis, there is a concentration of glycosaminoglycan present in the urine that deviates from the concentration in healthy patients, i.e., in patients with no detection of an interstitial cystitis. In this regard, it is also known that, in patients with a very advanced or chronic interstitial cystitis, the content of glycosaminoglycan in the urine is reduced in comparison with a control group with no detection, whereas the content of glycosaminoglycan in the urine in test subjects with interstitial cystitis in the initial stage or in the not very advanced stage is increased.

The tests and efficacy studies show that the best efficacy with regard to the treatment of the underlying disease in the form of interstitial cystitis exists for composition A1 in comparison with the further compositions, as stated above. In particular, a distinct improvement in well-being in terms of health can be observed, there being moreover in the test subjects of the group treated with composition A1 a virtually intact bladder mucus and moreover no lesions and no bleedings in the urothelium. Moreover, there is a distinct improvement in the glycosaminoglycan content. The tests thus show overall also the outstanding therapeutic efficacy of the inventive concept.

The invention claimed is:

1. A composition for the treatment of inflammatory diseases of the urogenital tract,
    wherein the composition comprises in combination and in effective amounts each:
    (a) at least one of chondroitin sulfate and a physiologically compatible chondroitin sulfate salt in a concentration of (20±2) mg/ml as component (a), wherein the chondroitin sulfate or the physiologically compatible chondroitin sulfate salt each have a weight-average molecular weight $M_w$ within the range of from 10 kDa to 200 kDa;
    (b) at least one of hyaluronic acid and a physiologically compatible hyaluronic acid salt (hyaluronate) in a concentration of (16±1.6) mg/ml as component (b), wherein the hyaluronic acid or the physiologically compatible hyaluronic acid salt each have a weight-average molecular weight $M_w$ within the range of from 10 kDa to 500 kDa;
    (c) a dihydrogen phosphate/monohydrogen phosphate buffer system as component (c), wherein the composition comprises the dihydrogen phosphate/monohydrogen phosphate buffer system in a total concentration of dihydrogen phosphate/monohydrogen phosphate buffer system of (1.75±1.65) mg/ml;
    wherein the composition is set to a pH value within the range of from 6.1 to 7.9.

2. The composition as claimed in claim 1,
    wherein the inflammatory diseases of the urogenital tract are selected among inflammatory diseases of the bladder and cystitis.

3. The composition as claimed in claim 1,
    wherein the composition comprises the dihydrogen phosphate/lmonohydrogen phosphate buffer system in a weight ratio of dihydrogen phosphate to monohydrogen phosphate within the range of from 2 : 1 to 1 : 100.

4. The composition as claimed in claim 1,
    wherein the dihydrogen phosphate/imonohydrogen phosphate buffer system is present as a $NaH_2(PO_4)$ / $Na_2H(PO_4)$ buffer system.

5. The composition as claimed in claim 1,
    wherein the composition further comprises at least one physiologically compatible electrolyte as component (d).

6. The composition as claimed in claim 5
    wherein the composition comprises the electrolyte in a concentration of (8 ±6) mg/ml.

7. The composition as claimed in claim 5
    wherein the electrolyte is present in the form of an alkali metal salt.

8. The composition as claimed in claim 5,
    wherein the electrolyte is present in the form sodium chloride.

9. Previously presented) The composition as claimed in claim 1,
    wherein the pH of the composition is set within the range of from 6.6 to 7.7.

10. The composition as claimed in claim 1,
    wherein the composition is storage-stable for a storage time point of at least 6 months at temperatures within the range of from 20 ° C. to 45 ° C., at a pressure of 1013.25 mbar and at a relative air humidity within the range of from 50% to 90%,
    wherein the composition has a total content of degradation products of components (a) and (b) of at most 5%, based on the total concentration of components (a) and (b), at the respective storage time point.

11. The composition as claimed in claim 1,
    wherein the composition, in a form ready for use, is present at a volume of (50±10) ml.

12. The composition as claimed in claim 1,
    wherein the composition, in a form ready for instillation into the bladder,is present at a volume of (50±10) ml.

13. The composition as claimed in claim 1,
    wherein the composition, in a form ready for use, is present with an active-ingredient amount of component (a) of (1000±100) mg and with an active-ingredient amount of component (b) of (800±80) mg.

14. A storage and application device for instillation or for topical application into the urogenital region,
    wherein the storage and application device comprises a composition as claimed in claim 1.

15. The storage and application device as claimed in claim 14, wherein the composition comprises:
    an active-ingredient amount of component (a) of (1000±75) mg,
    an active-ingredient amount of component (b) of (800±60) mg,
    component (c) in a totalamount of (87.5±85) mg,
    component (d) in an amount of (400±300) mg.

16. A kit in the form an instillation system for instillation into the urogenital region, comprising:
    (i) at least one storage and application device as claimed in claim 14,
    (ii) at least one instillation device connectable to the storage and application device.

17. The kit as claimed in claim 16,
    wherein the composition is present in the storage and application device in a form ready for use.

18. The kit as claimed in claim 16,
    wherein the instillation device comprises an instillation hose.

19. A method of treating a patient suffering from an inflammatory disease of the urogenital tract,
    wherein the method comprises the topical application, via instillation, of a composition as claimed in claim 16 into the urogenital region.

20. The method as claimed in claim 19,
    wherein the inflammatory disease of the urogenital tract is cystitis.

* * * * *